(12) United States Patent
Gijzen

(10) Patent No.: US 7,354,390 B1
(45) Date of Patent: Apr. 8, 2008

(54) SEED COAT SPECIFIC NUCLEOTIDE SEQUENCE ENCODING PEROXIDASE

(75) Inventor: Mark Gijzen, London (CA)

(73) Assignee: Her Majesty The Queen In Right Of Canada As Represented By The Minister Of Agriculture And Agri-Food, Ottawa, Ontario (CA)

( * ) Notice: Subject to any disclaimer, the term of this patent is extended or adjusted under 35 U.S.C. 154(b) by 0 days.

(21) Appl. No.: 08/939,905

(22) Filed: Sep. 29, 1997

Related U.S. Application Data

(63) Continuation-in-part of application No. 08/723,414, filed on Sep. 30, 1996, now abandoned.

(51) Int. Cl.
| | | |
|---|---|---|
| C07H 21/04 | (2006.01) | |
| C07H 21/02 | (2006.01) | |
| C12N 15/82 | (2006.01) | |
| C12Q 1/68 | (2006.01) | |
| C12N 1/20 | (2006.01) | |
| C12N 15/00 | (2006.01) | |
| C12N 5/02 | (2006.01) | |

(52) U.S. Cl. ............... 531/23.1; 435/6; 435/252.3; 435/320.1; 435/325; 536/24.1; 800/278; 800/287

(58) Field of Classification Search ............... 435/69.1, 435/6; 436/501; 536/23.1
See application file for complete search history.

(56) References Cited

U.S. PATENT DOCUMENTS

| 5,370,770 | A |  | 12/1994 | Johnson et al. ................. 162/6 |
| 5,491,085 | A |  | 2/1996 | Pokora et al. ............... 435/192 |
| 5,981,839 | A | * | 11/1999 | Knauf et al. ................. 800/287 |
| 6,586,583 | B1 | * | 7/2003 | Vierling, Jr. ............... 536/24.1 |
| 6,596,490 | B2 | * | 7/2003 | Dattagupta ..................... 435/6 |

FOREIGN PATENT DOCUMENTS

| JP | 04126088 | 9/1990 |
| WO | WO 95/08914 | 6/1995 |

OTHER PUBLICATIONS

Sigma Chemical 1990 Catalog [Publ by Sigma Chemical Company, P.O. Box 14508, St. Louis, Missouri, USA], p. 776, 1990.*
1990 Sigma Chemical Catalog [Published by Sigma Chemical Company, P.O. Box 14508, St. Louis, MO 63178 USA (1990)] pp. 776-778.*
BIOCHEMISTRY by Lehninger [Published by Worth Publishers, Inc. 70 Fifth Avenue, New York, New York 10011 (1970)], pp. 731-734.*
Gijzen et al., Plant Physiology, vol. 103, pp. 1061-1066, 1993.*
El-Iurk. J., Asemota, O., Leymarie, L. Sallaud, C. Mesnage, S , Breda, C. Buffard, D. Kondorosi, A. and Esnault, R. Nucleotide Sequences Of Four Pathogen-Induced Alfalfa Peroxidase-Encoding cDNAs, Journal Gene 170(2).213-216(1996).

Baga, M., Chibbar. R.N. and Kartha, K.K., Molecular Cloning And Expression Analysis Of Peroxidase Genes From Wheat, Journal Plant Mol. Biol. 29(4), 647-662 (1995), Accession No. X85228.
Osakabe, K., Koyama, H., Kawai, S., Katayama, Y. and Morohoshi, N., Molecular Cloning And Nucleotide Sequences Of Two Novel cDNA that Encode Anionic Peroxidases Of Populus Kitakmiensis, Journal Unpublished (1994), GenBank 1994, Accession No. D30652.
Abrahams, S.L., Hayes, C M. and Watson, J.M , Organ-Specific Expression Of Three Peroxidase-Encoding cDNAs From Lucerne (Medicago Sativa), Journal Unpublished (1994). GenBank Accession No. L36156.
Scott-Craig, J.S., Kerby, K.B., Stein, B.D. and Somerville, S C. Expression Of An Extracellular Peroxidase That Is Induced In Barley (Hordeum Vulgare) by the Powedery Mildew Pathogen (Erysiphe graminis f. sp. hrodei), Journal Unpublished (1994), Accession No. L36093.
Osakabe, K., Koyama, H., Kawai, S., Katayama, Y. and Morohoshi, N., Molecular Cloning And Nucleotide Sequences Of Two Novel cDNAs that Encode Anionic Peroxidases Of Populus Kitakamiensis, Journal Unpublished (1994), GenBank 1994, Accession No. D30653.
Osakabe, K., Kawai, S . Katayama, Y. and Morohoshi, N., Nucleotide Sequence For The Genomic DNA Encoding The Anionic Peroxidase Gene From Nicotiana Tabacum, Journal Unpublished (1993), GenBank 1993 Accession No. D11396.
Diaz-De-Leon, F., Klotz, K.L., and Lagrimini, M., Nucleotide Sequence Of The Tobacco (Nicotiana Tabacum) Anionic Peroxidase Gene, Journal Plant Physiol. 101, 1117-1118 (1993). Medline 94143471, Accession No. L02124.
Fujiyama, K., Takemura, H., Shibayama, S. Kobayashi, K., hoi. J.-K. Shinmyo, A., Takano, M., Yamada, Y., and Okada, H., Structure Of The Horseradish Peroxidase Isozyme c Genes, Journal Eur. J. Biochem. 173, 681-687 (1988), Medline 88225087, Accession No. M37156.
Huangpu et al. Cloning Of A Soybean cDNA Encoding The Abundant Anionic Seed Coat Peroxidase, Plant Gene Register PGR95-136, GenBank Accession No. U41657, 1995.
Osakabe et al. Molecular Cloning Of Two Tandemly Arranged Peroxidase Genes From Populus Kitakamiensis And Their Differential Regulation In The Stem, Plant Molecular Biology 28:677-689, 1995.
Gillikin and Graham, Purification And Developmental Analysis Of The Major Anionic Peroxidase From The Seed Coat Of Glycine MAX[1], Plant Physiol. (1991) 96, 214-220.

(Continued)

Primary Examiner—Shubo (Joe) Zhou
(74) Attorney, Agent, or Firm—Nixon & Vanderhye P.C.

(57) ABSTRACT

A novel seed coat specific peroxidase genomic sequence is characterized and presented. The seed coat peroxidase is translated as a 352 amino acid precursor protein of 38 kDa comprising a 26 amino acid signal sequence which when cleaved results in a 35 kDa protein. Probes derived from the cDNA, or genomic DNA can be used to detect polymorphisms that distinguish EpEp and epep genotypes. The regulatory region of the seed coat specific gene may be used to control expression of genes of interest such as genes encoding herbicide resistance, biological control of insects or pathogens, viral coat proteins to protect against viral infections, proteins of commercial interest, or proteins that alter the nutritive value, taste, or processing of seeds.

36 Claims, 15 Drawing Sheets

OTHER PUBLICATIONS

Lagrimini et al. Peroxidase-Induced Wilting In Transgenic Tobacco Plants, The Plant Cell, vol. 2, Jan. 7-18, 1990, American Society Of Plant Physiologists.

Gijzen et al. Soybean Seed Coat Peroxidase. A Comparison Of High-Activity And Low-Activity Genotypes, Plant Physiol. (1993) 103:1061-1066.

McEldoon et al. Lignin Peroxidase-Type Activity Of Soybean Peroxidase, Enzyme And Microbial Technology, 17:359-365, 1995.

Sessa et al. Soybean Peroxidases: Purification And Some Properties. J. Agric. Food Chem., vol. 29, No. 5, 1981, p. 960-965.

Freiberg, Indiana Crop: Keeping Its Members Up With The Changing Times, From Isozymes To Peroxidase, Seeds & Crops Ind. (Mar. 1995) pp. 4-9.

Mark Gijzen, A Deletion Mutation at the ep Locus causes low seed coat Peroxidase Activity in Soybean, Genbank ACC No. (GBN): AF014502, Aug. 25, 1997.

Buffard et al. "Molecular cloning of complementary DNAs encoding two cationic peroxidases from cultivated peanut cells" Proc. Natl. Acad. Sci. USA 87:8874-8878 (1990).

* cited by examiner

FIGURE 1A

```
                                    ATGGGTTCCATGCGTCTATT        20
                                     M  G  S  M  R  L  L

------ prx9+ ----->
AGTAGTGGCATTGTTGTGTGCATTTGCTATGCATGCAGGTTTTTCAGTCTCTTATGCTCA    80
 V  V  A  L  L  C  A  F  A  M  H  A  G  F  S  V  S  Y  A  Q     1
                          signal sequence GCTTACTCCTACGTTCTACAGAGAAACATGTCCAAATCTGTTCCCTATTGTGTTTGGAGT   140
 L  T  P  T  F  Y  R  E  T  C  P  N  L  F  P  I  V  F  G  V    21

------ prx12+ ---->
AATCTTCGATGCTTCTTTCACCGATCCCCGAATCGGGGCCAGTCTCATGAGGCTTCATTT   200
 I  F  D  A  S  F  T  D  P  R  I  G  A  S  L  M  R  L  H  F    41
                                              active site
               I                             <------
TCATGATTGCTTTGTTCAAG GTTGTGATGGATCAGTTTTGCTGAACAACACTGATACAAT   260
 H  D  C  F  V  Q  G  C  D  G  S  V  L  L  N  N  T  D  T  I    61

--prx10- ---        ------ prx2+ ----->
AGAAAGCGAGCAAGATGCACTTCCAAATATCAACTCAATAAGAGGATTGGACGTTGTCAA   320
 E  S  E  Q  D  A  L  P  N  I  N  S  I  R  G  L  D  V  V  N    81

TGACATCAAGACAGCGGTGGAAAATAGTTGTCCAGACACAGTTTCTTGTGCTGATATTCT   380
 D  I  K  T  A  V  E  N  S  C  P  D  T  V  S  C  A  D  I  L   101

II
TGCTATTGCAGCTGAAATAGCTTCTGTTCTG GCAGGAGGTCCAGGATGGCCAGTTCCATT   440
 A  I  A  A  E  I  A  S  V  L  G  G  G  P  G  W  P  V  P  L   121

AGGAAGAAGGGACAGCTTAACAGCAAACCGAACCCTTGCAAATCAAAACCTTCCAGCACC   500
 G  R  R  D  S  L  T  A  N  R  T  L  A  N  Q  N  L  P  A  P   141

TTTCTTCAACCTCACTCAACTTAAAGCTTCCTTTGCTGTTCAAGGTCTCAACACCCTTGA   560
 F  F  N  L  T  Q  L  K  A  S  F  A  V  Q  G  L  N  T  L  D   161

III
TTTAGTTACACTCTCAG GTGGTCATACGTTTGGAAGAGCTCGGTGCAGTACATTCATAAA   620
 L  V  T  L  S  G  G  H  T  F  G  R  A  R  C  S  T  F  I  N   181
     heme-binding domain CCGATTATACAACTTCAGCAACACTGGAAACCCTGATCCAACTCTGAACACAACATACTT   680
 R  L  Y  N  F  S  N  T  G  N  P  D  P  T  L  N  T  T  Y  L   201

AGAAGTATTGCGTGCAAGATGCCCCCAGAATGCAACTGGGGATAACCTCACCAATTTGGA   740
 E  V  L  R  A  R  C  P  Q  N  A  T  G  D  N  L  T  N  L  D   221

CCTGAGCACACCTGATCAATTTGACAACAGATACTACTCCAATCTTCTGCAGCTCAATGG   800
 L  S  T  P  D  Q  F  D  N  R  Y  Y  S  N  L  L  Q  L  N  G   241
```

FIGURE 1B

```
CTTACTTCAGAGTGACCAAGAACTTTTCTCCACTCCTGGTGCTGATACCATTCCCATTGT    860
 L   L   Q   S   D   Q   E   L   F   S   T   P   G   A   D   T   I   P   I   V     261

<----- prx6- ------
CAATAGCTTCAGCAGTAACCAGAATACTTTCTTTTCCAACTTTAGAGTTTCAATGATAAA    920
 N   S   F   S   S   N   Q   N   T   F   F   S   N   F   R   V   S   M   I   K     281

AATGGGTAATATTGGAGTGCTGACTGGGGATGAAGGAGAAATTCGCTTGCAATGTAATTT    980
 M   G   N   I   G   V   L   T   G   D   E   G   E   I   R   L   Q   C   N   F     301

TGTGAATGGAGACTCGTTTGGATTAGCTAGTGTGGCGTCCAAAGATGCTAAACAAAAGCT   1040
 V   N   G   D   S   F   G   L   A   S   V   A   S   K   D   A   K   Q   K   L     321

TGTTGCTCAATCTAAATAAACCAATAATTAATGGGGATGTGCATGCTAGCTAGCATGTAA   1100
 V   A   Q   S   K   *                                                              326

AGGCAAATTAGGTTGTAAACCTCTTTGCTAGCTATATTGAAATAAACCAAAGGAGTAGTG   1160

TGCATGTCAATTCGATTTTGCCATGTACCTCTTGGAATATTATGTAATAATTATTTGAAT   1220

CTCTTTAAGGTACTTAATTAATC(A)n
```

FIGURE 2A

```
            10         20         30         40         50         60
             |          |          |          |          |          |
   1 GCATCATATCATAAACAATACGTACGTGATATTATCTAGTGTCTCTCAGTTTACTTTATG
  61 AGAAATTATTTTTCTTTAAAAAAAGTTAATTAATAAAACATTTGCGATACCGTGAGTTA
 121 CAAGAAATCCGCCGAATTCATCTCTATAAATAAAAGGATCTATATGAGAGGTAAAATCAT
 181 ATTAACTCAAAATGGGTTCCATGCGTCTATTAGTAGTGGCATTGTTGTGTGCATTTGCTA
 241 TGCATGCAGGTTTTTCAGTCTCTTATGCTCAGCTTACTCCTACGTTCTACAGAGAAACAT
 301 GTCCAAATCTGTTCCCTATTGTGTTTGGAGTAATCTTCGATGCTTCTTTCACCGATCCCC
 361 GAATCGGGGCCAGTCTCATGAGGCTTCATTTTCATGATTGCTTTGTTCAAGTACGTACTT
 421 TTTTTTTTCCTTCCAAAATGCCCTGCATATTTAACAAGATTGCTTTGTTCACCTAGAAAA
 481 ATGTGTTTTTTTCAACGATCTTACGTACGTTTGTTTGGTTTGAAAAATAAATCAGAAAGA
 541 GATCAAGAAAATAGCTAGAAAGAAAGCAACGTTTTTTTAAAAGGTATTTAGTGTGAGAAA
 601 AATATTAAAACTGAAGAGAAAGAAATTAAATAAGCTTTTCTTGAATGATATTTACATGTC
 661 TTATTAACTTAAAGTCACCTTTTTTCTTTAAGTTGTGCTTGAAGAAAAAGATGTCTTTC
 721 AGTTTAGTTTTGATTAATGCTAATTATATTTTTAATTAATTAATTAATACTATATATCTA
 781 TTTACCATATTAATTATTACTATATTTCATGATGACAACAGACAAGTATTCTAAAGAGGT
 841 ATCGGTAGATGATTAATTTTTTTATAAAAAATCTTTTGCGTGTATAGATATTCTTTTAT
 901 AATTGGTGCAGAAACTTGTAATGCTAATTGCAATTAATCTTACATTGATTAACTAATAGC
 961 TATAATCAATATTTAGGTTAGGTATAGGAGACAAATCAAGTGATCTGAACAAATTAAGTT
1021 GTTATATTTGCATTGTGACAGGGTTGTGATGGATCAGTTTTGCTGAACAACACTGATACA
1081 ATAGAAAGCGAGCAAGATGCACTTCCAAATATCAACTCAATAAGACGATTGGACGTTGTC
1141 AATGACATCAAGACAGCGGTGGAAAATAGTTGTCCAGACACAGTTTCTTGTGCTGATATT
1201 CTTGCTATTGCAGCTGAAATAGCTTCTGTTCTGGTAATTAATAACTCCTAATTAATTCCC
1261 AACCATTAAAAAGTTGCATGATTGGATTCAAAATTCTATGGTATTGGGGTTCTGATATAA
1321 ATTTGTAATTAAATTGCACTAAAAAAAATTATCATATACTTTTAATAAAAAAATTTATC
1381 TAATTTAATTTATTATTAAAACTATTTTAAAATTCAATCCTAACTCTTTTTTAATCGGA
1441 GCATGTAAGCTGGCACCCACCGTATATCGTTGGAAGATGCTATAAAACCATTTAATTAAT
1501 GGATGGAATCAGTCAAAACATTTAATTCAAAATACTCTTAATTGTGATTAGTAATCATGT
1561 TCGGCAAGTTACGTTGTGTATAATTAATTTGACTTAATCAGATAAAAAAACAAATGGAC
1621 GCAAGCCGGTTGGTATAGATATCACTGGCCTGTAGAATATGTGGTTTTTCACGTTTAAAT
1681 AAAAGCTAGCTACTATATTATATTTAGTCTTTTTTTTTCTTAAACCCATTTAACGTGATT
1741 TATTGACTGTGAAACATGTTTCCACACACAGGCTTAGAAACTCCTCGCAACTAACATCTC
1801 CAAAATTTGACTATTTATTTATGAAGATAATTCATCTATGATGTTCAACTCTATTATATA
1861 TATGTATCATCGCAGTATTAAGAATTATAATAGTCAAATATAGAAGTATATCGGGTAAAT
1921 GTAGTTGCATGTGCGACCTGTTTCGTGTAAAATGCTTATTCTATATAGCTTTTTTTATTG
1981 GAAATAACGATGAACTAAAAACGAAGGGTATCATATAGTTTGACTTTTATGTTAGAGA
2041 GAGACATCTTAATTTGGTCATATGTTAAATAATTAATTACAATGCATACACAAATATTTA
2101 TGCCATATCTAAAAAATGATAAAATATCATAGGTATACTCAACTATATGATATCCCCATA
2161 ACAGAAATTGTACTTTTCTTCAGGCAATGAACTTAACATTTCTGTTTGCTAAAACAAAC
2221 ATCCACTTAAAGTGGTTCAACATATTTATGTAATAATTTACAGGGAGGAGGTCCAGGATG
```

FIGURE 2B

```
2281 GCCAGTTCCATTAGGAAGAAGGGACAGCTTAACAGCAAACCGAACCCTTGCAAATCAAAA
2341 CCTTCCAGCACCTTTCTTCAACCTCACTCAACTTAAAGCTTCCTTTGCTGTTCAAGGTCT
2401 CAACACCCTTGATTTAGTTACACTCTCAGGTATACATAATCAATTTTTTATTTGCTATTA
2461 GCTAGCAATAAAAAGTCTCTGATACAGACATATTTAGATAAATTAATTTCTCCATAAACA
2521 TTTATAATAAAATTATCAATTTATGTACTTAAAAATTATGGATTGAAGCTCTTTTCATCC
2581 AACTTTTACTAAAGTTAAGGTGCATATAATATAAAATAAACTATCTCTTGTTTCTTATAA
2641 AAAGATTGAAGATAAGTTAAAGTCTACTTATAAATCATTAATATATGTATAGGTGGTCAT
2701 ACGTTTGGAAGAGCTCGGTGCAGTACATTCATAAACCGATTATACAACTTCAGCAACACT
2761 GGAAACCCTGATCCAACTCTGAACACAACATACTTAGAAGTATTGCGTGCAAGATGCCCC
2821 CAGAATGCAACTGGGGATAACCTCACCAATTTGGACCTGAGCACACCTGATCAATTTGAC
2881 AACAGATACTACTCCAATCTTCTGCAGCTCAATGGCTTACTTCAGAGTGACCAAGAACTT
2941 TTCTCCACTCCTGGTGCTGATACCATTCCCATTGTCAATAGCTTCAGCAGTAACCAGAAT
3001 ACTTTCTTTTCCAACTTTAGAGTTTCAATGATAAAAATGGGTAATATTGGAGTGCTGACT
3061 GGGGATGAAGGAGAAATTCGCTTGCAATGTAATTTTGTGAATGGAGACTCGTTTGGATTA
3121 GCTAGTGTGGCGTCCAAAGATGCTAAACAAAAGCTTGTTGCTCAATCTAAATAAACCAAT
3181 AATTAATGGGGATGTGCATGCTAGCTAGCATGTAAAGGCAAATTAGGTTGTAAACCTCTT
3241 TGCTAGCTATATTGAAATAAACCAAAGGAGTAGTGTGCATGTCAATTCGATTTTGCCATG
3301 TACCTCTTGGAATATTATGTAATAATTATTTGAATCTCTTTAAGGTACTTAATTAATCA
```

FIGURE 3A-(1)

```
L78163    --------------ATGGGTTCCATGCGT-CTATTAGTAGTGGCATTGTTG    36
U41657    ------------------------------------------------    0
X90693    G----GCAAA-CAATGAACTCCCTTCGTGCTGTAGCAATAG-CTTTGTGC    44
X90694    GCTCTTCAAAACAATGAACTCC---------TTAGCAACTT-CTATGTGG    40
L36156    ------------------CTCC---------TTAGCAACTT-CTATGTGG    22
X90692    -------AATGCTTGGT-----CTAAGTGCAACAGCTTTTTGCTGTATGG    38

L78163    TGT-----GCATTT-GCTATGCATGCAGGTTTTTCAGT---CTCTTATGC    77
U41657    ------------------------------------------------    0
X90693    TGTATTGTG------GTTGTGCTTGGAGGGTTACCCTTCTCTTCAAATGC    88
X90694    TGTGTTGTGCTTTTAGTTGTGCTTGGAGGACTACCCTTTTCCTCAGATGC    90
L36156    TGTGTTGTGCTTTTAGTTGTGCTTGGAGGACTACCCTTTTCCTCAGATGC    72
X90692    TGT-TTGTGCTAAT--------TGGAGGAGTACCCTTTT---CAAATGC    75

L78163    TCAGCTTACTCCTACGTTCTACAGAGAAACATGTCCAAATCTGTTCCCTA    127
U41657    ------------------------------------------------    0
X90693    GCAACTTGATCCATCCTTTTACAGGAACACTTGTCCAAATGTTAGTTCCA    138
X90694    ACAACTTAGTCCCACTTTTTACAGCAAAACGTGTCCAACTGTTAGTTCCA    140
L36156    ACAACTTAGTCCCACTTTTTACAGCAAAACGTGTCCAACTGTTAGTTCCA    122
X90692    ACAACTAGATCCTTCATTTTACAACAGTACATGTTCTAATCTTGATTCAA    125

L78163    TTGTGTTTGGAGTAATCTTCGATGCTTCTTTCACCGATCCCCGAATCGGG    177
U41657    ------------------------------------------------    0
X90693    TTGTTCGTGAAGTCATAAGGAGTGTTTCTAAGAAAGATCCTCGTATGCTT    188
X90694    TTGTTAGCAATGTCTTAACAAACGTTTCTAAGACAGATCCTCGCATGCTT    190
L36156    TTGTTAGCAATGTCTTAACAAACGTTTCTAAGACAGATCCTCGCATGCTT    172
X90692    TCGTACGTGGTGTGCTCACAAATGTTTCACAATCTGATCCCAGAATGCTT    175

L78163    GCCAGTCTCATGAGGCTTCATTTTCATGATTGCTTTGTTCAAGGTTGTGA    227
U41657    --------------------TTTCATGATTGCTTTGTTCAAGGTTGTGA    29
X90693    GCTAGTCTTGTCAGGCTTCACTTTCATGACTGTTTTGTTCAAGGTTGTGA    238
X90694    GCTAGTCTCGTCAGGCTTCACTTTCATGACTGTTTTGTTCTGGGATGTGA    240
L36156    GCTAGTCTCGTCAGGCTTCACTTTCATGACTGTTTTGTTCTGGGATGTGA    222
X90692    GGTAGTCTCATCAGGCTACATTTTCATGACTGTTTTGTTCAAGGTTGCGA    225
                              ******** ** *******..**.** **

L78163    TGGATCAGTTTTGCTGAACAACACTGATACAATAGAAAGCGAGCAAGATG    277
U41657    TGGATCAGTTTTACTGAACAACACTGATACAATAGAAAGCGAGCAAGATG    79
X90693    TGCATCAGTTTTACTAAACAAAACTGATACCGTTGTGAGTGAACAAGATG    288
X90694    TGCCTCAGTTTTGCTGAACAATACTGCTACAATCGTAAGCGAACAACAAG    290
L36156    TGCCTCAGTTTTGCTGAACAATACTGCTACAATCGTAAGCGAACAACAAG    272
X90692    TGCCTCGATTTTGCTGAACGATACGGCTACAATAGTGAGCGAGCAAAGTG    275
          **  **..****.**.***.*  **.*  *** .*  *.  ** **.***  ..*

L78163    CACTTCCAAATATCAACTCAATAAGAGGATTGGACGTTGTCAATGACATC    327
U41657    CACTTCCAAATATCAACTCAATAAGAGGATTGGACGTTGTCAATGACATC    129
X90693    CTTTTCCAAACAGAAACTCATTAAGAGGTTTGGATGTTGTGAATCAAATC    338
X90694    CTTTTCCAAATAACAACTCTCTAAGAGGTTTGGATGTTGTGAATCAGATC    340
L36156    CTTTTCCAAATAACAACTCTCTAAGGGGTTTGGATGTTGTGAATCAGATC    322
X90692    CACCACCAAATAACAACTCCATAAGAGGTTTGGATGTGATAAACCAGATC    325
          *.  .*****  *.  ***** **.*****.** *****.** **.* ***
```

FIGURE 3A-(2)

```
L78163    AAGACAGCGGTGGAAAATAGTTGTCCAGACACAGTTTCTTGTGCTGATAT    377
U41657    AAGACAGCGGTGGAAAATAGTTGTCCAGACACAGTTTCTTGTGCTGATAT    179
X90693    AAAACAGCTGTGGAAAAGGCTTGTCCTAACACAGTTTCTTGTGCTGATAT    388
X90694    AAACTGGCTGTAGAAGTGCCTTGTCCTAACACAGTTTCTTGTGCTGATAT    390
L36156    AAAACTGCTGTAGAAAGTGCTTGTCCTAACACAGTTTCTTGTGCTGATAT    372
X90692    AAAACAGCGGTGGAAAATGCTTGTCCTAACACAGTTTCTTGTGCTGATAT    375
          **. .**.**.***   ***** .*********************

L78163    TCTTGCTATTGCAGCTGAAATAGCTTCTGTT-CTGGGAGGAGGTCCAGGA    426
U41657    TCTTGCTATTGCAGCTGAAATAGCTTCTGTTGCTGGGAGGAGGTC-AGGA    228
X90693    TCTTGCTCTTTCTGCTGAATTATCATCTACA-CTGGCAGATGGTCCTGAC    437
X90694    TCTTGCACTTGCTGCTCAAGCATCCTCTGTT-CTGGCACAAGGTCCTAGT    439
L36156    TCTTGCACTTGCT---CAAGCATCCTCTGTT-CTGGCACAAGGTCCTAGT    418
X90692    TCTTGCTCTTTCTGCTGAAATATCATCTGAT-CTGGCAAATGGTCCTACT    424
          ****** .**.*.    **.*.*.***.. .**** * ..****. ..

L78163    TGGCCAGTTCCATTAGGAAGAAGGGACAGCTTAACAGCAAACCGAACCCT    476
U41657    TGGCCAGTTCCATTAGGAAGAAGGGACAGCTTAACAGCAAACCGAACCCT    278
X90693    TGGAAGGTTCCTTTAGGAAGAAGAGATGGTTTAACGGCAAACCAGTTACT    487
X90694    TGGACGGTTCCTTTAGGAAGAAGGGATGGTTTAACCGCAAACCGAACACT    489
L36156    TGGACGGTTCCTTTAGGAAGAAGGGATGGTTTAACCGCAAACCGAACACT    468
X90692    TGGCAAGTTCCATTAGGAAGAAGGGATAGTTTGACAGCAAATAATTCCCT    474
          *** .*****.*************.** .* **.** *****  ... **

L78163    TGCAAATCAAAACCTTCCAGCACCTTTCTTCAA--CCTCA-CTCAACTTA    523
U41657    TGCAAATCAAAACCTTCCAGCACCTTTCTTCAA--CCTCA-CTCAACTTA    325
X90693    TGCTAATCAAAATCTTCCAGCTCC---TTTCAATACTACTGATCAACTTA    534
X90694    TGCAAATCAAAATCTTCCGGCTCC---ATTCAATTCCTTGGATCAACTTA    536
L36156    TGCAAATCAAAATCTTCCGGCTCC---ATTCAATTCCTTGGATCACCTTA    515
X90692    TGCAGCTCAAAATCTTCCTGCCCCACTTTCAA--CCTTA-CTCGACTAA    521
          ***.. ****** ***** ** **      *****  *  . **.**.*

L78163    AAGCTTCCTTTG-CTGTTCAAGGTCTCAACACCCTTGATTTAGTTACACT    572
U41657    AAGCTTCCTTTG-CTGTTCAAGGTCTCAACACCCTTGATTTAGTTACACT    374
X90693    AAGCTGCATTTG-CTGCTCAAGGTCTCGATACTACTGATCTGGTTGCACT    583
X90694    AAGCTGCATTT-ACTGCTCAAGGCCTCAATACTACTGATCTAGTTGCACT    585
L36156    AA-CTGCATTTGACTGCTCAAGGCCTCATTACTCCTGTTCTAGTTGCCCT    564
X90692    AATCTAACTTTGA-TAATCAAAACCTCAGTACTACTGATCTAGTTGCACT    570
          ** **. ***   *. ****.. ***. .**  .** * *** * **

L78163    CTCAGGTGGTCATACGTTTGGAAGAGCTCGGTGCAGTACATTCATAAACC    622
U41657    CTCAGGTGGTCATACGTCTGGAAGAGCTCGGTGCAGTACATTCATAAACC    424
X90693    CTCCGGTGCTCATACATTTGGAAGAGCTCATTGCTCTTTATTTGTTAGCC    633
X90694    CTCGGGTGCTCATACATTTGGAAGAGCTCATTGCGCACAATTTGTTAGTC    635
L36156    CTCGGGTGCTCATACATTTGGAAGAGCTCATTGCGCACAATTTGTTAGTC    614
X90692    CTCAGGTGGCCATACAATTGGAAGAGGTCAATGCAGATTTTTCGTTGATC    620
          *** ****  *****. ******** **..***. . .** .*...  *

L78163    GATTATACAACTTCAGCAACACTGGAAACCCTGATCCAACTCTGAACACA    672
U41657    GATTATACAACTTCAGCAACACTGGA----CTGATCCA-CT-TGGACACA    468
X90693    GATTGTACAACTTCAGCGGTACGGGAAGTCCCGATCCAACTCTTAACACA    683
X90694    GATTGTACAACTTCAGCAGTACTGGAAGTCCCGATCCAACTCTTAACACA    685
L36156    GATTGTACAACTTCAGCAGTACTGGAAGTCCCGATCCAACTCTTAACACA    664
X90692    GATTATACAATTTCAGCAACACTGGAAACCCCGATTCAACTCTTAACACG    670
          ****.*****. ***** ..*** **   ** *** ** ** ** ****.
```

FIGURE 3A-(3)

```
L78163    ACATACTTAGAAGTATTGCGTGCAAGATGCCCCCAGAATGCAACTGGGGA    722
U41657    ACATACTTAGAAGTATTGCGTGCAAGATGCCCCCAGAATGCAACTGGGGA    518
X90693    ACTTACTTACAACAATTGCGCACAATATGTCCCAATGGTGGACCTGGCAC    733
X90694    ACTTACTTACAACAACTGCGCACAATATGTCCCAATGGTGGACCTGGCAC    735
L36156    ACTTACTTACAACAACTGCGCACAATATGTCCCAATGGTGGACCTGGCAC    714
X90692    ACCTATTTACAAACATTGCAAGCAATATGTCCCAATGGTGGACCTGGTAC    720
          ** ** *** **   * ***. ***.*** ***  *...** * ****  .

L78163    TAACCTCACCAATTTGGACCTGAGCACACCTGATCAATTTGACAACAGAT    772
U41657    TAACCTCACCAATTTGGACCTGAGCACACCTGATCAATTTGACAACAGAT    568
X90693    GAACCTTACCAATTTCGATCCAACGACTCCTGATAAATTTGACAAGAACT    783
X90694    AAACCTTACCAATTTCGATCCAACGACTCCTGATAAATTTGACAAGAACT    785
L36156    AAACCTTACCAATTTCGATCCAACGACTCCTGATAAATTTGACAAGAACT    764
X90692    AAACCTAACCGATTTGGACCCAACCACACCAGATACATTTGACTCCAACT    770
           .***** ***.****  **  *    *   **.**.*** *******. *. *

L78163    ACTACTCCAATCTTCTGCAGCTCAATGGCTTACTTCAGAGTGACCAAGAA    822
U41657    ACTACTCCAATCTTCTGCAGCTCAATGGCTTACTTCAGAGTGACCAAGAA    618
X90693    ATTACTCTAATCTTCAAGTGAAAAAAGGTTTGCTTCAAAGTGATCAAGAG    833
X90694    ATTACTCCAATCTTCAAGTGAAAAAGGGTTTGCTCCAAAGTGATCAAGAG    835
L36156    ATTACTCCAATCTTCAAGTGAAAAAGGGTTTGCTCCAAAGTGATCAAGAG    814
X90692    ACTACTCCAATCTCCAAGTTGGAAAGGGCTTGTTTCAGAGTGACCAAGAG    820
          * ***** *****  *..  ..  . **.** **. * **.***** *****.

L78163    CTTTTCTCCACTCCTGGTGCTGATACCATTCCCATTGTCAATAGCTTCAG    872
U41657    CGTTTCTCCACTCCTGGTGCTGATACCATTCC-ATTGTCAATAGCTTCAG    667
X90693    TTGTTCTCAACATCTGGTTCAGATACCATTAGCATTGTCAACAAATTCGC    883
X90694    TTGTTCTCAACTTCTGGTGCAGATACCATTAGCATTGTCAACAAATTCAG    885
L36156    TTGTTCTCAACTTCTGGTGCAGATACCATTAGCATTGTCGACAAATTCAG    864
X90692    CTTTTTTCCAGAAATGGTTCTGACACTATTTCTATTGTCAATAGTTTCGC    870
          . .** ** * .  ****.*.** ** ***   ****** .* *. ***.

L78163    CAGTAACCAGAATACTTTCTTTTCCAACTTTAGAGTTTCAATGATAAAAA    922
U41657    CG--AACCAGAATACTTTCTTTTCCAACTTTAGAGTTTCAATGATAAAAA    715
X90693    AACCGATCAAAAAGCTTTTTTTGAGAGCTTTAGGGCTGCTATGATCAAAA    933
X90694    CACCGATCAAAATGCTTTCTTTGAGAGCTTTAAGGCTGCAATGATTAAAA    935
L36156    CACCGATCAAAATGCTTTCTTTGAGAGCTTTAAGGCTGCAATGATTAAAA    914
X90692    CAATAATCAAACTCTCTTCTTTGAAAATTTTGTAGCCTCAATGATAAAAA    920
           .  * **.*    ** ***. *. ***... *  *.***** ****

L78163    TGGGTAATATTGGAGTGCTGACTGGGGATGAAGGAGAAATTCGCTTGCAA    972
U41657    TGGGTAATATTGGAGTGCTGACTGGGGATGAAGGAGAAATTCGCTTGCAA    765
X90693    TGGGAAATATTGGTGTGTTAACCGGGAACCAAGGAGAGATTAGAAAACAA    983
X90694    TGGGCAATATTGGTGTGCTAACAGGGACAAAAGGAGAGATTAGAAAACAA    985
L36156    TGGGCAATATTGGTGTGCTAACAGGGACAAAAGGAGAGATTAGAAAACAA    964
X90692    TGGGTAATATTGGAGTTTTAACTGGATCTCAAGGTGAAATTAGAACACAG    970
          ****  ********.**  *.** **.. .  ****.**.***  *  .**.

L78163    TGTAATTTTGTGAA---TGGAGACTCGT-----------TTGGATTAGC    1007
U41657    TGTAATTTTGTGAA---TGGAGACTCGT-----------TTGGATTAGC    800
X90693    TGCAACTTTGTTAATT--------CAAAATCAGCAGAACTTGGTCTTAT    1024
X90694    TGCAACTTTGTGAACTTTGTGAACTCAAATTCTGCAGAACTAGATTTAGC    1035
L36156    TGCAACTT--------TGTGAACTCAAATTCTGCAGAACTAGATTTAGC    1005
X90692    TG--------TAATGCTGTGAATGGGAATTCTTC------TGGATTGGC    1005
          **                                    .*.. *..
```

FIGURE 3A-(4)

```
L78163    TAGTGTGGCGTCCAAAGATGCTAAACAAAAGCTTGTTGCTCAATCTAAAT    1057
U41657    TAGTGTGGCGTCCAAAGATGCTAAACAAAAGCTTGTTGCTCAATCTAAAT     850
X90693    CAATGTTGCCTC---AGCAG--ATTCATCTG-AGGAGGGTATGGTTAG--    1066
X90694    CACCATAGCATCCATAGTAG--AATCATTAG-AGGATGGTATTGCTAGTG    1082
L36156    CACCATAGCATCCATAGTAG--AATCATTAG-AGGATGGAATTGCTAGTG    1052
X90692    TACTGTAGTCACCAA---AG--AATCATCAG-AAGATGGAATGGCTAGCT    1049
           *  .*.*  .*        .*  *..**..*  ..*..*  ....  **.

L78163    AAACCAATAATTAATGGGGATGTGCATGCTAGCTAGCATGTAAAGGCAAA    1107
U41657    AAACCAATAATTAATGGGGATGTCGATGCTAGCTACGATGTAAAGGCAAA     900
X90693    -----------------------------------CTCAATGTAAA-TG-TAG    1082
X90694    TAATATAAATAAATTAG------CGTAAATGCACTTATTGAA-ATCTTG    1124
L36156    TAATATAAATAAATTAG------CGAAAATGCACTTATTGAA-ATCTTG    1094
X90692    CATTCTAAAT--ATAAG------CTTGGAAAATATTGAAGAGGTTCTAT    1090
                                              . ....*. .. ...

L78163    TTAGGTTGTAAACCTCTTTGCTAGCTATATTGAAATAAACCAAAGGAGTA    1157
U41657    TTAGGTTG-AAACCTCTTTGCTAGCTATATTGAAATAAACCAAAGGAGTA     949
X90693    T--GATTGGAAGCAACTAA--TAAATTAAGAAGCTATAAC---------T    1119
X90694    T--GACTAGATGCCACTAA--TAAAT----AAGTTATAAC---------T    1157
L36156    T--GACTAGATCCCACTAA--TAAAT----AAGTTATAAC---------T    1127
X90692    A--ATTTTGTGCATACATA--TATGGTATGTG------------------    1118
           .  ..*. ..  .*...  **.  .       ..

L78163    GTGTGCATGTCAATTCGATTTTGC-CATGTACCTCTTGGAATAT------    1200
U41657    GTGTCGATGTCAATTCGATTTTGC-CATGTACCTCTTGGAATATTATGTA     998
X90693    ATGCACATT-CATGGTATGTGTGAGATAGTTATTAGATGCTTTGTGAGCA    1168
X90694    AGGCACATTTCATGTCACTTGAATTTCATGCCT-GTATATGAG------    1200
L36156    AGGCACATTTCATGTCACTTGAAATCCTATGCCTTGTATATTAGAGGACG    1177
X90692    -----CATGTGGTGTA--TTATGTTTTGTTATGTTCTTCAAGTTGATCA    1161
          **.      ....     .*...     .*.    .  ..  ....

L78163    --------------------------------    1200
U41657    ATAATTATTTGAATCTC-------AAAAAAAAAAAAAAAA    1031
X90693    AAAATCTTTTGGATTTC----ATTTGAAGTGTTTCT----    1200
X90694    --------------------------------    1200
L36156    TGT-TCTT--------C------TTGGTATTATACTA--T    1200
X90692    GGGA-CTGTAGAAGCTCCCTAATAATATTTGTGTCAAAGT    1200
```

FIGURE 3B

```
L78163    MGSMRLLVVALLCAFAMHAGFSVSY---AQLTPTFYFETCPNLFPIVEGV      47
U41657    ------------------------------------------------         0
X90693    MNSLRAVAIALCCIV--VVLGGLPFSSNAQLDPSFYFNTCPNVSSIVREV      48
X90694    MNSL---ATSMWCVVLLVVLGGLPFSSDAQLSPTFYSKTCPTVSSIVSNV      47
L36156    M---------WCVVLLVVLGGLPFSSDAQLSPTFYSKTCPTVSSIVSNV       40
X90692    MLGLSATA---FCCMVFVLIGGVPFS-NAQLDPSFYNSTCSNLDSIVRGV      46

L78163    IFDASFTDPPIGASLMRLHFHDCFVQGCDGSVLLNNTDTIESEQDALFHI      97
U41657    ------------------FHDCFVQGCDGSVLLNNTDTIESEQDALFHI      31
X90693    IRSVSKKDPRMLASLVRLHFHDCFVQGCDASVLLNKTDTVVSEQDAFPHR      98
X90694    LTNVSKTDPRMLASLVRLHFHDCFVLGCDASVLLNNTATIVSEQQAFPHN      97
L36156    LTNVSKTDPRMLASLVRLHFHDCFVLGCDASVLLNNTATIVSEQQAFPHN      90
X90692    LTNVSQSDPRMLGSLIRLHFHDCFVQGCDASILLNDTATIVSEQSAPFHN      96
                          ****** *** * *** * * *** * **

L78163    NSIRGLDVVNDIKTAVENSCPDTVSCADILAIAAEIASVLGGGPGWPVPL     147
U41657    NSIRGLDVVNDIKTAVENSCPDTVSCADILAIAAEIASVAGRRSGWPVPL      81
X90693    NSLRGLDVVNQIKTAVEKACPNTVSCADILALSAELSSTLADGPDWKVPL     148
X90694    NSLRGLDVVNQIKLAVEVPCPNTVSCADILALAAQASSVLAQGPSWTVPL     147
L36156    NSLRGLDVVNQIKTAVESACPNTVSCADILALA-QASSVLAQGPSWTVPL     133
X90692    NSIRGLDVINQIKTAVENACPNTVSCADILALSAEISSDLANGPTWQVPL     146
          ** *****  * ***  ** ********** .  *       * ***

L78163    GRRDSLTANRTLANQNLPAPFFNLTQLKASFAVQGLNTLDLVTLSGGHTF     197
U41657    GRRDSLTANRTLANQNLPAPFFNLTQLKASFAVQGLNTLDLVTLSGGHTS     131
X90693    GRRDGLTANQLLANQNLPAPFNTTDQLKAAFAAQGLDTTDLVALSGAHTF     198
X90694    GRRDGLTANRTLANQNLPAPFNSLDQLKAAFTAQGLNTTDLVALSGAHTF     197
L36156    GRRDGLTANRTLANQNLPAPFNSLDHLKLHLTAQGLITPVLVALSGAHTF     189
X90692    GRRDSLTANNSLAAQNLPAPTFNLTRLFSNFDNQNLSTTDLVALSGGHTI     196
          ****.****. ** *****   *  *   . *  *  * . *****.**

L78163    GRARCSTFINRLYNFSNTGNPDPTLNTTYLEVLFAPCPQNATGDNLTNLD     247
U41657    GRARCSTFINRLYNFSNTGLIN--LDTTYLEVLFAPCPQNATGDNLTNLD     179
X90693    GRAHCSLFVSRLYNFSGTGSPDPTLNTTYLQQLFTICPNGGPGTNLTNFD     248
X90694    GRAHCAQFVSRLYNFSSTGSPDPTLNTTYLQQLFTICPNGGPGTNLTNFD     247
L36156    GRAHCAQFVSRLYNFSSTGSPDPTLNTTYLQQLFTICPNGGPGTNLTNFD     239
X90692    GRGQCRFFVDRLYNFSNTGNFDSTLNTTYLQTLQAICPNGSPGTNLTDLD     246
          ** . *    ****** **    *** *** . *  ** .    ***  *

L78163    LSTPDQFDNRYYSNLLQLNGLLQSDQELFSTPGADTIPIVNSFSSNQNTF     297
U41657    LSTPDQFDNRYYSNLLQLNGLLQSDQERFSTPGADTIPLSIA-SANQNTF     228
X90693    PTTPDKFDKNYYSNLQVKKGLLQSDQELFSTSGSDTISIVNKFATDQKAF     298
X90694    PTTPDKFDKNYYSNLQVKKGLLQSDQELFSTSGADTISIVNKFSTDQNAF     297
L36156    PTTPDKFDKNYYSNLQVKKGLLQSDQELFSTSGADTISIVNKFSTDQNAF     289
X90692    PTTPDTFDSNYYSNLQVGKGLFQSDQELFSRNGSDTISIVNSFANNQTLF     296
            *** **  *****    **.**** **  *.**     *     *

L78163    FSNFRVSMIKMGNIGVLTGDEGEIRLQCNFVN-----GDSFGLASVAS-K     341
U41657    FSNFRVSMIKMGNIGVLTGDEGEIPLQCNFVN-----GDSFGLASVAS-K     272
X90693    FESFRAAMIKMGNIGVLTGNQGEIPFQCNFVN---SKSAELGLINVAS-A     344
X90694    FESFKAAMIKMGNIGVLTGTKGEIPRQCNFVNFVNSNSAELDLATIASIV     347
L36156    FESFKAAMIKMGNIGVLTGTFGEIPFQCNFVN---SNSAELDLATIASIV     336
X90692    FENFVASMIKMGNIGVLTGSQGEIRTQCNAVN-----GNSSGLATVVT-K     340
          * .*   **********   ***  ***  **       .    .

L78163    DAKQKLVAQSK        352
U41657    DAKQKLVAQSK        283
X90693    DSSEEGMVSSM        355
X90694    ESLEDGIASVI        358
L36156    ESLEDGIASVI        347
X90692    ESSEDGMASSF        351
``` pr x 12+ / pr x 10-
765 bp pr x 9+ / pr x 10-
860 bp pr x 29+ / pr x 10-
1076 bp
989 bp

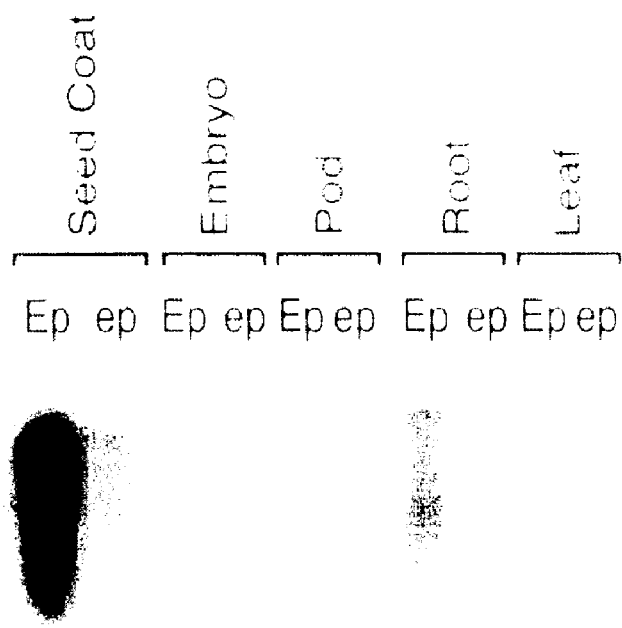
FIGURE 9A
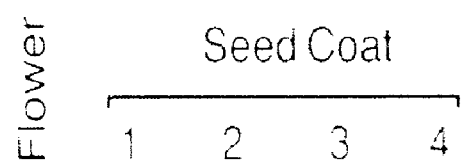
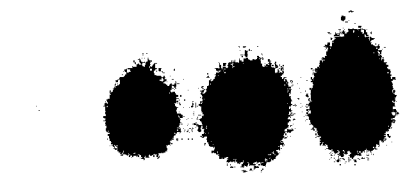
FIGURE 9B

SEED COAT SPECIFIC NUCLEOTIDE SEQUENCE ENCODING PEROXIDASE

This application is a continuation-in-part of application Ser. No. 08/723,414, filed Sep. 30, 1996 now abandoned.

The present invention relates to a novel DNA molecule comprising a plant seed coat specific DNA regulatory region and a novel structural gene encoding a peroxidase. The seed-coat specific DNA regulatory region may also be used to control the expression of other genes of interest within the seed coat.

BACKGROUND OF THE INVENTION

Full citations for references appear at the end of the Examples section.

Peroxidases are enzymes catalyzing oxidative reactions that use $H_2O_2$ as an electron acceptor. These enzymes are widespread and occur ubiquitously in plants as isozymes that may be distinguished by their isoelectric points. Plant peroxidases contribute to the structural integrity of cell walls by functioning in lignin biosynthesis and suberization, and by forming covalent cross-linkages between extension, cellulose, pectin and other cell wall constituents (Campa, 1991). Peroxidases are also associated with plant defence responses and resistance to pathogens (Bowles, 1990; Moerschbacher 1992). Soybeans contain 3 anionic isozymes of peroxidase with a minimum $M_r$ of 37 kDa (Sessa and Anderson, 1981). Recently one peroxidase isozyme, localised within the seed coat of soybean, has been characterized with a $M_r$ of 37 kDa (Gillikin and Graham, 1991).

In an analysis of soybean seeds, Buttery and Buzzell (1968) showed that the amount of peroxidase activity present in seed coats may vary substantially among different cultivars. The presence of a single dominant gene Ep causes a high seed coat peroxidase phenotype (Buzzell and Buttery, 1969). Homozygous recessive epep plants are ~100-fold lower in seed coat peroxidase activity. This results from a reduction in the amount of peroxidase enzyme present, primarily in the hourglass cells of the subepidermis (Gijzen et al., 1993). In plants carrying the Ep gene, peroxidase is heavily concentrated in the hourglass cells (osteosclereids). These cells form a highly differentiated cell layer with thick, elongated secondary walls and large intercellular spaces (Baker et al., 1987). Hourglass cells develop between the epidermal macrosclereids and the underlying articulated parenchyma, and are a prominent feature of seed coat anatomy at full maturity. The cytoplasm exudes from the hourglass cells upon imbibition with water and a distinct peroxidase isozyme constitutes five to 10% of the total soluble protein in EpEp seed coats. It is not known why the hourglass cells accumulate large amounts of peroxidase, but the sheer abundance and relative purity of the enzyme in soybean seed coats is significant because peroxidases are versatile enzymes with many commercial and industrial applications. Studies of soybean seed coat peroxidase have shown this enzyme to have useful catalytic properties and a high degree of thermal stability even at extremes of pH (McEldoon et al., 1995). These properties result in the preferred use of soybean peroxidase, over that of horseradish peroxidase, in diagnostic assays as an enzyme label for antigens, antibodies, oligonucleotide probes, and within staining techniques. Johnson et al report on the use of soybean peroxidase for the deinking of printed waste paper (U.S. Pat. No. 5,270,770; Dec. 6, 1994) and for the biocatalytic oxidation of primary alcohols (U.S. Pat. No. 5,391,488; Feb. 13, 1996). Soybean peroxidase has also been used as a replacement for chlorine in the pulp and paper industry, or as formaldehyde replacement (Freiberg, 1995).

An anionic soybean peroxidase from seed coats has been purified (Gillikin and Graham, 1991). This protein has a pI of 4.1 and $M_r$ of 37 kDa. A method for the bulk extraction of peroxidase from seed hulls of soybean using a freeze thaw technique has also been reported (U.S. Pat. No. 5,491,085, Feb. 13, 1996, Pokara and Johnson).

Lagrimini et al (1987) disclose the cloning of a ubiquitous anionic peroxidase in tobacco encoding a protein of $M_r$ of 36 kDa. This peroxidase has also been over expressed in transgenic tobacco plants (Lagrimini et al 1990) and Maliyakal discloses the expression of this gene in cotton (WO 95/08914).

Huangpu et al (1995) reported the partial cloning of a soybean anionic seed coat peroxidase. The 1031 bp sequence contained an open reading frame of 849 bp encoding a 283 amino acid protein with a $M_r$ of 30,577. The $M_r$ of this peroxidase is 7 kDa less than what one would expect for a soybean seed coat peroxidase as reported by Gillikin and Graham (1991) and possibly represents another peroxidase isozyme within the seed coat.

The upstream promoter sequences for two poplar peroxidases have been described by Osakabe et al (1995). A number of characteristic regulatory sites were identified from comparison of these sequences to existing promoter elements. Additionally, a cryptic promoter with apparent specificity for seed coat tissues was isolated from tobacco by a promoter trapping strategy (Fobert et al. 1994). The upstream regulatory sequences associated with the Ep gene in soybean are distinct from these and other previously characterized promoters. The soybean Ep promoter drives high-level expression in a cell and tissue specific manner. The peroxidase protein encoded by the Ep gene accumulates in the seed coat tissues, especially in the hour glass cells of the subepidermis. Minimal expression of the gene is detected in root tissues.

One problem arising from the desired use of soybean seed coat peroxidase is that there is variability between soybean varieties regarding peroxidase production (Buttery and Buzzell, 1986; Freiberg, 1995). Due to the commercial interest in the use of soybean seed coat peroxidase new methods of producing this enzyme are required. Therefore, the gene responsible for the expression of the 37 kDa isozyme in soybean seed coat was isolated and characterized.

Furthermore, novel regulatory regions obtained from the genomic DNA of soybean seed coat peroxidase have been isolated and characterized and are useful in directing the expression of genes of interest in seed coat tissues.

SUMMARY OF THE INVENTION

The present invention relates to a DNA molecule that encodes a soybean seed coat peroxidase and associated DNA regulatory regions.

This invention also embraces isolated DNA molecules comprising the nucleotide sequence of either SEQ ID NO: 1 (the cDNA encoding soybean seed coat peroxidase) or SEQ ID NO:2 (the genomic sequence).

This invention also provides for a chimeric DNA molecule comprising a seed coat-specific regulatory region having nucleotides 1-1532 of SEQ ID NO:2 and a gene of interest under control of this DNA regulatory region. Also included within this invention are chimeric DNA molecules comprising genomic DNA sequences exemplified by nucleotides 1752-2382, 2575-3604 or 3770-4032 of SEQ ID NO:2. Furthermore, this invention is directed to isolated DNA molecules comprising at least
1) 24 contiguous nucleotides selected from nucleotides 1752-2382 of SEQ ID NO:2;
2) 32 contiguous nucleotides selected from nucleotides 2575-3604 of SEQ ID NO:2;
3) 23 contiguous nucleotides selected from nucleotides 2575-3604 of SEQ ID NO:2; or
4) 22 contiguous nucleotides selected from nucleotides 3770-4032 of SEQ ID NO:2.

The present invention also provides for vectors which comprise DNA molecules encoding soybean seed coat peroxidase. Such a construct may include the DNA regulatory region from SEQ ID NO:2, including nucleotides 1-1532, or at least 24 contiguous nucleotides selected from nucleotides 1-1532 of SEQ ID NO:2 in conjunction with the seed coat peroxidase gene, or the seed coat peroxidase gene under the control of any suitable constitutive or inducible promoter of interest.

This invention is also directed towards vectors which comprise a gene of interest placed under the control of a DNA regulatory element derived from the genomic sequence encoding soybean seed coat peroxidase. Such a regulatory element includes nucleotides 1-1532 of SEQ ID NO:2, or at least 24 contiguous nucleotides selected from nucleotides 1-1532 of SEQ ID NO:2. Elements comprising nucleotides 1752-2382, 2575-3604 or 3770-4032 of SEQ ID NO:2, or 32 contiguous nucleotides selected from nucleotides 1752-2382 of SEQ ID NO:2, 23 contiguous nucleotides selected from nucleotides 2575-3604 of SEQ ID NO:2, or 22 contiguous nucleotides selected from nucleotides 3770-4032 of SEQ ID NO:2 may also be used.

This invention also embraces prokaryotic and eukaryotic cells comprising the vectors identified above. Such cells may include bacterial, insect, mammalian, and plant cell cultures.

This invention also provides for transgenic plants comprising the seed coat peroxidase gene under control of constitutive or inducible promoters. Furthermore, this invention also relates to transgenic plants comprising the DNA regulatory regions of nucleotides 1-1532 of SEQ ID NO:2 controlling a gene of interest, or comprising genes of interest in functional association with genomic DNA sequences exemplified by nucleotides 1752-2382, 2575-3604 or 3770-4032 of SEQ ID NO:2. Also embraced by this invention are transgenic plants having regulatory regions comprising at least 24 contiguous nucleotides selected from nucleotides 1-1532 of SEQ ID NO:2, 32 contiguous nucleotides selected from nucleotides 1752-2382 of SEQ ID NO:2, 23 contiguous nucleotides selected from nucleotides 2575-3604 of SEQ ID NO:2, or 22 contiguous nucleotides selected from nucleotides 3770-4032 of SEQ ID NO:2.

This invention is also directed to a method for the production of soybean seed coat peroxidase in a host cell comprising:
  i) transforming the host cell with a vector comprising an oligonucleotide sequence that encodes soybean seed coat peroxidase; and
  ii) culturing the host cell under conditions to allow expression of the soybean seed coat peroxidase.

This invention also provides for a process for producing a heterologous gene of interest within seed coats of a transformed plant, comprising propagating a plant transformed with a vector comprising a gene of interest under the control of nucleotides 1-1532 of SEQ ID NO:2. Furthermore, this invention embraces a process for producing a heterologous gene of interest within seed coats of a transformed plant, comprising propagating a plant transformed with a vector comprising a gene of interest under the control of a regulatory region comprising at least 24 nucleotides selected from nucleotides 1-1532 of SEQ ID NO:2.

Although the present invention is exemplified by a soybean seed coat peroxidase and adjacent DNA regulatory regions, in practice any gene of interest can be placed downstream from the DNA regulatory region for seed coat specific expression.

BRIEF DESCRIPTION OF THE DRAWINGS

These and other features of the invention will become more apparent from the following description in which reference is made to the appended drawings wherein:

FIGS. 1A and 1B are the cDNA and deduced amino acid sequence of soybean seed coat peroxidase (SEQ ID NO:1). Nucleotides are numbered by assigning +1 to the first base of the ATG start codon; amino acids are numbered by assigning +1 to the N-terminal Gln residue after cleavage of the putative signal sequence. The N-terminal signal sequence, the region of the active site, and the heme-binding domain are underlined. The numerals I, II and III placed directly above single nucleotide gaps in the sequence indicate the three intron splice positions. The target site and direction of five different PCR primers are shown with dotted lines above the nucleotide sequence. An asterisk (*) marks the translation stop codon.

FIGS. 2A and 2B are the genomic DNA sequence of the Soybean seed coat peroxidase (commencing at nucleotide 1342 of SEQ ID NO:2).

FIG. 3 is a comparison of soybean seed coat peroxidase with other closely related plant peroxidases. The GENBANK database accession numbers are provided next to the name of the plant from which the peroxidase was isolated. The accession number for the soybean sequence is L78163. (A) A comparison of the nucleic acid sequences; (B) A comparison of the amino acid sequences.

(FIG. 8A) Forward and reverse primers are downstream from deletion (FIG. 8B) Forward primer anneals to site within deletion (FIG. 8C) Primers span deletion FIGS. 9A and 9B show the accumulation of peroxidase RNA in tissues of GEp and epep plants. FIG. 9(A): A comparison of peroxidase transcript abundance in cultivars Harosoy 63 (Ep) or Marathon (ep). Seed and pod tissues were sampled at a late stage of development corresponding to a whole seed fresh weight of 250 mg. Root and leaf tissue was from six week old plants. Autoradiograph exposed for 96 h. FIG. 9(B): Developmental expression of peroxidase in cultivar Harosoy 63 (EP). Flowers were sampled immediately after opening. Seed coat tissues were sampled at four stages of development corresponding to a whole seed fresh weight of: lane 1, 50 mg; lane 2, 100 mg; lane 3, 200 mg; lane 4, 250 mg. Autoradiograph exposed for 20 h.

DESCRIPTION OF PREFERRED EMBODIMENT

Figure 4:
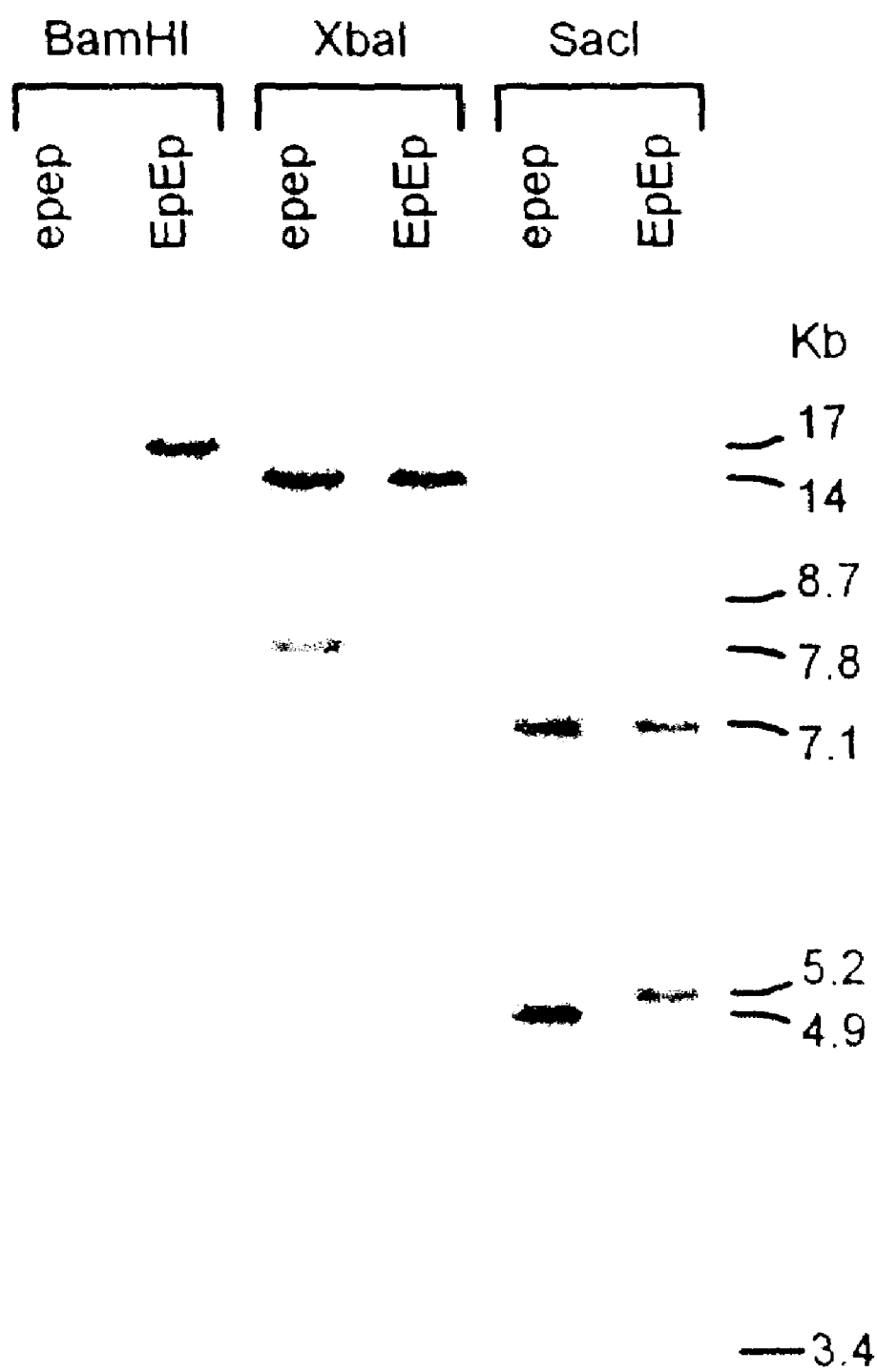
FIG. 4 is a restriction fragment length polymorphisms between EpEp and epep genotypes using the seed coat peroxidase cDNA as probe. Genomic DNA of soybean lines OX312 (epep) and OX347 (EpEp) was digested with restriction enzyme, separated by electrophoresis in a 0.5% agarose gel, transferred to nylon, and hybridized with $^{32}$P-labelled cDNA encoding the seed coat peroxidase. The size of the hybridizing fragments was estimated by comparison to standards and is indicated on the right.

The present invention is directed to a novel oligonucleotide sequence encoding a seed coat peroxidase and associated DNA regulatory regions.

According to the present invention DNA sequences that are "substantially homologous" includes sequences that are identified under conditions of high stringency. "High stringency" refers to Southern hybridization conditions employing washes at 65° C. with 0.1×SSC, 0.5% SDS.

By "DNA regulatory region" it is meant any region within a genomic sequence that has the property of controlling the expression of a DNA sequence that is operably linked with the regulatory region. Such regulatory regions may include promoter or enhancer regions, and other regulatory elements recognized by one of skill in the art. A segment of the DNA regulatory region is exemplified in this invention, however, as is understood by one of skill in the art, this region may be used as a probe to identify surrounding regions involved in the regulation of adjacent DNA, and such surrounding regions are also included within the scope of this invention.

In the context of this disclosure, the term "promoter" or "promoter region" refers to a sequence of DNA, usually upstream (5') to the coding sequence of a structural gene, which controls the expression of the coding region by providing the recognition for RNA polymerase and/or other factors required for transcription to start at the correct site.

There are generally two types of promoters, inducible and constitutive. An "inducible promoter" is a promoter that is capable of directly or indirectly activating transcription of one or more DNA sequences or genes in response to an inducer. In the absence of an inducer the DNA sequences or genes will not be transcribed. Typically the protein factor, that binds specifically to an inducible promoter to activate transcription, is present in an inactive form which is then directly or indirectly converted to the active form by the inducer. The inducer can be a chemical agent such as a protein, metabolite, growth regulator, herbicide or phenolic compound or a physiological stress imposed directly by heat, cold, salt, or toxic elements or indirectly through the action of a pathogen or disease agent such as a virus. A plant cell containing an inducible promoter may be exposed to an inducer by externally applying the inducer to the cell or plant such as by spraying, watering, heating or similar methods.

By "constitutive promoter" it is meant a promoter that directs the expression of a gene throughout the various parts of a plant and continuously throughout plant development. Examples of known constitutive promoters include those associated with the CaMV 35S transcript and Agrobacterium Ti plasmid nopaline synthase gene.

The chimeric gene constructs of the present invention can further comprise a 3' untranslated region. A 3' untranslated region refers to that portion of a gene comprising a DNA segment that contains a polyadenylation signal and any other regulatory signals capable of effecting mRNA processing or gene expression. The polyadenylation signal is usually characterized by effecting the addition of polyadenylic acid tracks to the 3' end of the mRNA precursor. Polyadenylation signals are commonly recognized by the presence of homology to the canonical form 5' AATAAA-3' although variations are not uncommon.

Examples of suitable 3' regions are the 3' transcribed non-translated regions containing a polyadenylation signal of Agrobacterium tumour inducing (Ti) plasmid genes, such as the nopaline synthase (Nos gene) and plant genes such as the soybean storage protein genes and the small subunit of the ribulose-1,5-bisphosphate carboxylase (ssRUBISCO) gene. The 3' untranslated region from the structural gene of the present construct can therefore be used to construct chimeric genes for expression in plants.

The chimeric gene construct of the present invention can also include further enhancers, either translation or transcription enhancers, as may be required. These enhancer regions are well known to persons skilled in the art, and can include the ATG initiation codon and adjacent sequences. The initiation codon must be in phase with the reading frame of the coding sequence to ensure translation of the entire sequence. The translation control signals and initiation codons can be from a variety of origins, both natural and synthetic. Translational initiation regions may be provided from the source of the transcriptional initiation region, or from the structural gene. The sequence can also be derived from the promoter selected to express the gene, and can be specifically modified so as to increase translation of the mRNA.

To aid in identification of transformed plant cells, the constructs of this invention may be further manipulated to include plant selectable markers. Useful selectable markers include enzymes which provide for resistance to an antibiotic such as gentamycin, hygromycin, kanamycin, and the like. Similarly, enzymes providing for production of a compound identifiable by colour change such as GUS (β-glucuronidase), or luminescence, such as luciferase are useful.

Also considered part of this invention are transgenic plants containing the chimeric gene construct of the present invention. Methods of regenerating whole plants from plant cells are known in the art, and the method of obtaining transformed and regenerated plants is not critical to this invention. In general, transformed plant cells are cultured in an appropriate medium, which may contain selective agents such as antibiotics, where selectable markers are used to facilitate identification of transformed plant cells. Once callus forms, shoot formation can be encouraged by employing the appropriate plant hormones in accordance with known methods and the shoots transferred to rooting medium for regeneration of plants. The plants may then be used to establish repetitive generations, either from seeds or using vegetative propagation techniques.

The constructs of the present invention can be introduced into plant cells using Ti plasmids, Ri plasmids, plant virus vectors, direct DNA transformation, micro-injection, electroporation, etc. For reviews of such techniques see for example Weissbach and Weissbach (1988) and Geierson and Corey (1988). The present invention further includes a suitable vector comprising the chimeric gene construct.

Buttery and Buzzell (1968) showed that the amount of peroxidase activity present in seed coats may vary substantially among different cultivars. The presence of a single dominant gene Ep causes a high seed coat peroxidase phenotype (Buzzell and Buttery, 1969). Homozygous recessive epep plants are ~100-fold lower in seed coat peroxidase activity. This results from a reduction in the amount of peroxidase enzyme present, primarily in the hourglass cells of the subepidermis (Gijzen et al., 1993). In plants carrying the Ep gene, peroxidase is heavily concentrated in the hourglass cells (osteosclereids). These cells form a highly differentiated cell layer with thick, elongated secondary walls and large intercellular spaces (Baker et al., 1987).

Screening a seed coat cDNA library prepared from EpEp plants with a degenerate primer derived from the active site domain of plant peroxidase resulted in a high frequency of positive clones. Many of these clones encode identical cDNA molecules and indicate that the corresponding mRNA is an abundant transcript in developing seed coat tissues. The sequence of the cDNA is shown in FIG. 1.

Previous studies on soybean seed coat peroxidase indicated that this enzyme is heavily glycosylated and that carbohydrate contributes 18% of the mass of the apo-enzyme (Gray et al., 1996). The seven potential glycosylation sites identified from the amino acid sequence of the seed cost peroxidase (FIG. 1) would accommodate the five or six N-linked glycosylation sites proposed by Gray et al. (1996). The heme-binding domain encompasses residues Asp161 to Phe171 and the acid-base catalysis region from Gly33 to Cys44. The two regions are highly conserved among plant peroxidases and are centred around functional histidine residues, His169 and His40. There are eight conserved cysteine residues in the mature protein that provide for four di-sulfide bridges found in other plant peroxidases and predicted from the crystal structure of peanut peroxidase (Welinder, 1992; Schuller et al., 1996). Other conserved areas include residues Cys91 to Ala105 and Val119 to Leu127 that occur in or around helix D. The most divergent aspects of the seed coat peroxidase protein sequence are the carboxy- and amino-terminal regions. These sequences probably provide special targeting signals for the proper processing and delivery of the peptide chain. It is possible the carboxy-terminal extension of the seed coat peroxidase is removed at maturity, as has been shown for certain barley and horseradish peroxidases (Welinder, 1992).

The molecular mass of the enzyme has been determined by denaturing gel electrophoresis to be 37 kDa (Sessa and Anderson, 1981; Gillikin and Graham, 1991) or 43 kDa (Gijzen et al., 1993). Analysis by mass spectrometry indicated a mass of 40,622 Da for the apo-enzyme and 33,250 Da after deglycosylation (Gray et al., 1996). These values are in good agreement with the mass of 35,377 Da calculated from the predicted amino acid sequence for the mature apo-protein prior to glycosylation and other modifications. Huangpu et al (1995) reported an anionic seed coat peroxidase having a $M_r$ of 30,577 Da and characterized a partial cDNA encoding this protein. This 1031 bp cDNA contained an open reading frame of 849 bp encoding a 283 amino acid protein. There are several differences between this reported sequence and the sequence of this invention that are manifest at the amino acid level (see FIG. 3 for sequence comparison). The enzyme encoded by the gene reported by Huangpu et al is different from that of this invention as the peroxidase of this invention has a $M_r$ of 35,377 Da.

Genomic DNA blots probed with the seed coat peroxidase cDNA produced two or three hybridizing fragments of varying intensity with most restriction enzyme digestions, despite that several peroxidase isozymes are present in soybean. The results indicate that this seed coat peroxidase is present as a single gene that does not share sufficient homology with most other peroxidase genes to anneal under conditions of high stringency.

The genomic DNA sequence comprises four exons spanning bp 1533-1752 (exon I), 2383-2574 (exon 2), 3605-3769 (exon 3) and 4033-4516 (exon 4) and three introns comprising 1752-2382 (intron 1), 2575-3604 (intron 2) and 3770-4032 (intron 3), of SEQ ID NO:2. Features of the upstream regulatory region of the genomic DNA include a TATA box centred on bp 1487; a cap signal 32 bp down stream centred on bp 1520. Also noted within the genomic sequence are three polyadenylation signals centred on bp 4520, 4598, 4663 and a polyadenylation site at bp 4700.

This promoter is considered seed coat specific since the peroxidase protein encoded by the Ep gene accumulates in the seed coat tissues, especially in the hourglass cells of the subepidermis, and is not expressed in other tissues, aside from a marginal expression of peroxidase in the root tissues. This is also true at the transcriptional level (see FIG. 9). The DNA regulatory regions of the genomic sequence of FIG. 2 are used to control the expression of the adjacent peroxidase gene in seed coat tissue. Such regulatory regions include nucleotides 1-1532. Other regions of interest include nucleotides 1752-2382, 2575-3604 and/or 3770-4032 of SEQ ID NO:2. Therefore other proteins of interest may be expressed in seed coat tissues by placing a gene capable of expressing the protein of interest under the control of the DNA regulatory elements of this invention. Genes of interest include but are not restricted to herbicide resistant genes, genes encoding viral coat proteins, or genes encoding proteins conferring biological control of pest or pathogens such as an insecticidal protein for example *B. thuringiensis* toxin. Other genes include those capable of the production of proteins that alter the taste of the seed and/or that affect the nutritive value of the soybean.

A modified DNA regulatory sequence may be obtained by introducing changes into the natural sequence. Such modifications can be done through techniques known to one of skill in the art such as site-directed mutagenesis, reducing the length of the regulatory region using endonucleases or exonucleases, increasing the length through the insertion of linkers or other sequences of interest. Reducing the size of DNA regulatory region may be achieved by removing 3' or 5' regions of the regulatory region of the natural sequence by using a endonuclease such as BAL 31 (Sambrook et al 1989). However, any such DNA regulatory region must still function as a seed coat specific DNA regulatory region.

It may be readily determined if such modified DNA regulatory elements are capable of acting in a seed coat specific manner transforming plant cells with such regulatory elements controlling the expression of a suitable marker gene, culturing these plants and determining the expression of the marker gene within the seed coat as outlined above. One may also analyze the efficacy of DNA regulatory elements by introducing constructs comprising a DNA regulatory element of interest operably linked with an appropriate marker into seed coat tissues by using particle bombardment directed to seed coat tissue and determining the degree of expression of the regulatory region as is known to one of skill in the art.

Two tandemly arranged genes encoding anionic peroxidase expressed in stems of *Populus kitakamiensis*, prxA3a and prxA4a have been cloned and characterized (Osakabe et al, 1995). Both of these genomic sequences contained four exons and three introns and encoded proteins of 347 and 343 amino acids, respectively. The two genes encode distinct isozymes with deduced $M_r$s of 33.9 and 34.6 kDa. Furthermore, a 532 bp promoter derived from the peroxidase gene of *Armoracia rusticana* has also been reported (Toyobo KK, JP 4,126,088, Apr. 27, 1992).

However, a search using GenBank revealed no substantial similarity between the promoter region, or introns 1, 2 and 3 of this invention and those within the literature.

Digestion of the genomic DNA with BamHI or SacI revealed restriction fragment length polymorphisms that distinguished EpEp and epep genotypes. Although the XbaI digestion did not produce a readily detectable polymorphism, the size of the hybridizing fragment in both genotypes was ~14 kb. Thus, a 0.3 kb size difference is outside of the resolving power of the separation for fragments this large. Sequence analysis of EpEp and epep genotypes indicates that the mutant ep allele is missing 87 bp of sequence at the 5' end of the structural gene. This would account for the drastically reduced amounts of peroxidase enzyme present in seed coats of epep plants since the deletion includes the translation start codon and the entire N-terminal signal sequence. However, the 87 bp deletion cannot account for the differences observed in the RFLP analysis since the missing fragment does not include a BamHI site and is much smaller than the 0.3 kb polymorphism detected in the SacI digestion. Thus, other genetic rearrangements must occur in the vicinity of the ep locus that lead to these polymorphisms.

The results shown here indicate that the mutation causing low seed coat peroxidase activity occurs in the structural gene encoding the enzyme. This mutation is an 87 bp deletion in the 5' region of the gene encompassing the translation start site. Several different low peroxidase cultivars share a similar mutation in the same area, suggesting that the recessive ep alleles have a common origin or that the region is prone to spontaneous deletions or rearrangements.

Due to the industrial interest in soybean seed coat peroxidase, alternate sources for the production of this enzyme are needed. The DNA of this invention, encoding the seed coat soybean peroxidase under the control of a suitable promoter and expressed within a host of interest, can be used for the preparation of recombinant soybean seed coat peroxidase enzyme.

Soybean seed coat peroxidase has been characterized as a lignin-type peroxidase that has industrially significant properties ie: high activity and stability under acidic conditions; exhibits wide substrate specificity; equivalent catalytic properties to that of *Phanerochaete chrysosporium* ligin peroxidase (the currently preferred enzyme used for treatment of industrial waste waters (Wick 1995) but is at least 150-fold more stable; more stable than horseradish peroxidase which is also used in industrial effluent treatments and medical diagnostic kits (McEldoon et al., 1995). These properties are useful within industrial applications for the degradation of natural aromatic polymers including lignin and coal (McEldoon et al, 1995), and the preferred use of soybean peroxidase, over that of horseradish peroxidase, in medical diagnostic tests as an enzyme label for antigens, antibodies, oligonucleotide probes, and within staining techniques (Wick 1995). Soybean peroxidase is also used in the deinking of printed waste paper (Johnson et al., U.S. Pat. No. 5,270,770; Dec. 6, 1994) and for the biocatalytic oxidation of primary alcohols (Johnson et al., U.S. Pat. No. 5,391,488; Feb. 13, 1996). Soybean peroxidase has also been used as a replacement for chlorine in the pulp and paper industry, in order to remove chlorine, phenolic or aromatic amine containing pollutants from industrial waste waters (Wick 1995), or as formaldehyde replacement (Freiberg, 1995) for use in adhesives, abrasives, and protective coatings (e.g. varnish and resins, Wick 1995).

Furthermore, the seed coat peroxidase gene may be expressed in an organ or tissue specific manner within a plant. For example, the quality and strength of cotton fibber can be improved through the over-expression of cotton or horseradish peroxidase placed under the control of a fibre-specific promoter (Maliyakal, WO 95/08914; Apr. 6, 1995).

Similarly, seed-specific DNA regulatory regions of this invention may be used to control expression of genes of interest such as:

i) genes encoding herbicide resistance, or ii) biological control of insects or pathogens (e.g. *B. thuringiensis*), or iii) viral coat proteins to protect against viral infections, or iv) proteins of commercial interest (e.g. pharmaceutical), and v) proteins that alter the nutritive value, taste, or processing of seeds within the seed coat of plants.

While this invention is described in detail with particular reference to preferred embodiments thereof, said embodiments are offered to illustrate but not to limit the invention.

EXAMPLES

Plant Material

All soybean (Glycine max [L.] Merr) cultivars and breeding lines were from the collection at Agriculture Canada, Harrow, Ontario.

Seed Coat cDNA Library Construction and Screening

High seed coat peroxidase (EpEp) soybean cultivar Harosoy 63 plants were grown in field plots outdoors. Pods were harvested 35 days after flowering and seeds in the mid-to-late developmental stage were excised. The average fresh mass was 250 mg per seed. Seed coats were dissected and immediately frozen in liquid nitrogen. The frozen tissue was lyophilized and total RNA extracted in 100 mM Tris-HCl pH 9.0, 20 mM EDTA, 4% (w/v) sarkosyl, 200 mM NaCl, and 16 mM DTT, and precipitated with LiCl using the standard phenol/chloroform method described by Wang and Vodkin (1994). The poly(A)+ RNA was purified on oligo (dT) cellulose columns prior to cDNA synthesis, size selection, ligation into the λ ZAP Express vector, and packaging according to instructions (Stratagene). A degenerate oligonucleotide with the 5' to 3' sequence of TT(C/T)CA(C/T)GA(C/T)TG(C/T)TT(C/T)GT (SEQ ID NO:3) was 5' end labelled to high specific activity and used as a probe to isolate peroxidase cDNA clones (Sambrook et al., 1989). Duplicate plaque lifts were made to nylon filters (Amersham), UV fixed, and prehybridized at 36° C. for 3 h in 6×SSC, 20 mM $Na_2HPO_4$ (pH6.8), 5×Denhardt's, 0.4% SDS, and 500 μg/mL salmon sperm DNA. Hybridization was in the same buffer, without Denhardt's, at 36° C. for 16 h. Filters were washed quickly with several changes of 6×SSC and 0.1% SDS, first at room temperature and finally at 40° C., prior to autoradiography for 16 h at −70° C. with an intensifying screen.

Genomic DNA Isolation, Library Construction, and DNA Blot Analysis

Soybean genomic DNA was isolated from leaves of greenhouse grown plants or from etiolated seedlings grown in vermiculite. Plant tissue was frozen in liquid nitrogen and lyophilized before extraction and purification of DNA according to the method of Dellaporta et al. (1983). Restriction enzyme digestion of 30 μg DNA, separation on 0.5% agarose gels and blotting to nylon membranes followed standard protocols (Sambrook et al., 1989). For construction of the genomic library, DNA purified from Harosoy 63 leaf tissue was partially digested with BamHI and ligated into the λ FIX II vector (Stratagene). GIGAPACK XL packaging extract (Stratagene) was used to select for inserts of 9 to 22 kb. After library amplification, duplicate plaque lifts were hybridized to cDNA probe.

Blots or filter lifts were prehybridized for 2 h at 65° C. in 6×SSC, 5×Denhardt's, 0.5% SDS, and 100 μg/mL salmon sperm DNA. Radiolabelled cDNA probe (20 to 50 ng) was prepared using the Ready-to-Go labelling kit (Pharmacia) and $^{32}$P-dCTP (Amersham). Unincorporated $^{β2}$P-dCTP was removed by spin column chromatography before adding radiolabelled cDNA to the hybridization buffer (identical to prehybridization buffer without Denhardt's). Hybridization was for 20 h at 65° C. Membranes were washed twice for 15 min at room temperature with 2×SSC, 0.5% SDS, followed by two 30 min washes at 65° C. with 0.1×SSC, 0.5% SDS. Autoradiography was for 20 h at −70° C. using an intensifying screen and X-OMAT film (Kodak).

DNA Sequencing

Sequencing of DNA was performed using dye-labelled terminators and Taq-FS DNA polymerase (Perkin-Elmer). The PCR protocol consisted of 25 cycles of a 30 sec melt at 96° C., 15 sec annealing at 50° C., and 4 min extension at 60° C. Samples were analyzed on an Applied Biosystems 373A Stretch automated DNA sequencer.

Polymerase Chain Reaction

PCR amplifications contained 1 ng template DNA, 5 pmol each primer, 1.5 mM $MgCl_2$, 0.15 mM deoxynucleotide triphosphates mix, 10 mM Tris-HCl, 50 mM KCl, pH 8.3, and 1 unit of Taq polymerase (Gibco BRL) in a total volume of 25 μL. Reactions were performed in a Perkin-Elmer 480 thermal cycler. After an initial 2 min denaturation at 94° C., there were 35 cycles of 1 min denaturation at 94° C., 1 min annealing at 52° C., and 2 min extension at 72° C. A final 7 min extension at 72° C. completed the program. The following primers were used for PCR analysis of genomic DNA:

prx2+ CTTCCAAATATCAACTCAAT (SEQ ID NO:4)

prx6− TAAAGTTGGAAAAGAAGTA (SEQ ID NO:5)

prx9 ATGCATGCAGGTTTTTCAGT (SEQ ID NO:6)

prx10− TTGCTCGCTTTCTATTGTAT (SEQ ID NO:7)

prx12+ TCTTCGATGCTTCTTTCACC (SEQ ID NO:8)

prx29+ CATAAACAATACGTACGTGAT (SEQ ID NO:9)

RNA Isolation

For isolation of RNA, tissue was harvested from greenhouse grown plants, dissected, frozen in liquid nitrogen, and lyophilized prior to extraction. Total RNA was purified from seed coats, embryos, pods, leaves, and flowers using standard phenol/chloroform method (Sambrook et al., 1989). This method did not afford good yields of RNA from roots, therefore this tissue was extracted with TRIZOL isothiocyanate reagent (GibcoBRL) and total RNA purified according to manufacturers' instructions with an additional phenol-chloroform extraction step. The amount of RNA was estimated by measuring absorbance at 260 and 280 nm, and by electrophoretic separation in formaldehyde gels followed by staining with ethidium bromide and comparison to known standards. Total RNA (10 μg per sample) was prepared, subject to electrophoresis through a 1% agarose gel containing formaldehyde, and then stained with ethidium bromide to ensure equal loading of samples. The gel was blotted to nylon membrane (HYBOND N, Amersham) according to standard methods and the RNA was fixed to the membrane by UV cross linking.

Seed Coat Peroxidase Assays

The $F_3$ seed was measured for peroxidase activity to score the phenotype of the $F_2$ population because the seed testa is derived from maternal tissue. The seeds were briefly soaked in water and the seed coat was dissected from the embryo and placed in a vial. Ten drops (~500 μL) of 0.5% guaiacol was added and the sample was left to stand for 10 min before adding one drop (~50 μL) of 0.1% $H_2O_2$. An immediate change in colour of the solution, from clear to red, indicates a positive result and high seed coat peroxidase activity.

Example 1

The Seed Coat Peroxidase cDNA and Genomic DNA Sequences

To isolate the seed coat peroxidase transcript, a cDNA library was constructed from developing seed coat tissue of the EpEp cultivar Harosoy 63. The primary library contained $10^6$ recombinant plaque forming units and was amplified prior to screening. A degenerate 17-mer oligonucleotide corresponding to the conserved active site domain of plant peroxidases was used to probe the library. In screening 10,000 plaque forming units, 12 positive clones were identified. The cDNA insert size of the clones ranged from 0.5 to 2.5 kb, but six clones shared a common insert size of 1.3 kb. These six clones (soyprx03, soyprx05, soyprx06, soyprx11, soyprx12, and soyprx14) were chosen for further characterization since the 1.3 kb insert size matched the expected peroxidase transcript size. Sequence analysis of the six clones showed that they contained identical cDNA transcripts encoding a peroxidase and that each resulted from an independent cloning event since the junction between the cloning vector and the transcript was different in all cases.

Since it was not clear that the entire 5' end of the cDNA transcript was complete in any of the cDNA clones isolated, the structural gene corresponding to the seed coat peroxidase was isolated from a Harosoy 63 genomic library. A partial BamHI digest of genomic DNA was used to construct the library and more than $10^6$ plaque forming units were screened using the cDNA probe. A positive clone, G25-2-1-1-1, containing a 17 kb insert was identified and a 4.7 kb region encoding the peroxidase was sequenced SEQ ID NO:2. This region includes 1532 nucleotides of the 5' region of the peroxidase gene.

The genomic sequence matched the cDNA sequence except for three introns encoded within the gene. The genomic sequence also revealed two additional translation start codons, beginning one bp and 10 bp upstream from the 5' end of the longest cDNA transcript isolate. FIG. 1 (SEQ ID NO:1) shows the deduced cDNA sequence. The open reading frame of 1056 bp encodes a 352 amino acid protein of 38,106 Da. A heme-binding domain, a peroxidase active site signature sequence, and seven potential N-glycosylation sites were identified from the deduced amino acid sequence. The first 26 amino acid residues conform to a membrane spanning domain. Cleavage of this putative signal sequence releases a mature protein of 326 residues with a mass of 35,377 Da and an estimated pI of 4.4.

Relevant features of the genomic fragment (FIG. 2) include four exons at bp 192-411 (exon 1; 1533-1751 of SEQ ID NO:2), 1042-1233 (exon 2; 2383-2574 of SEQ ID NO:2), 2263-2429 (exon 3; 4033-4516 for SEQ ID NO:2) and 2692-3174 (exon 4; 1752-2382 of SEQ ID NO:2) and three introns at bp 412-1041 (intron 1; 1752-2382 of SEQ ID NO:2), 1234-2263 (intron 2; 2575-3604 of SEQ ID NO:2) and 2430-2691 (intron 3; 37704032 of SEQ ID NO:2). The 1532 bp regulatory region of the genomic DNA include a TATA box centred on bp 1487 and a cap signal 32 bp down stream centred at bp 1520 of SEQ ID NO:2. Also noted within the genomic sequence are three polyadenylation signals centred on bp 4520, 4598, 4700 and a polyadenylation site at bp 4700 of SEQ ID NO:2.

FIG. 3 (SEQ ID Nos:10-19) illustrates the relationship between the soybean seed coat peroxidase and other selected plant peroxidases. The soybean sequence is most closely related to four peroxidase cDNAs isolated from alfalfa, (see FIG. 3) sharing from 65 to 67% identity at the amino acid level with the alfalfa proteins (X90693, X90694, X90692, el-Turk et al 1996; L36156, Abrahams et al 1994). When compared with other plant peroxidases, soybean seed coat peroxidase exhibits from 60 to 65% identity with poplar (D30653 and D30652, Osakabe et al 1994)) and flax (L0554, Omann and Tyson 1995); 50 to 60% identity with horseradish (M37156, Fujiyama et al. 1988), tobacco (D11396, Osakabe et al 1993), and cucumber (M91373, Rasmussen et al. 1992); and 49% identity with barley (L36093, Scott-Craig et al. 1994), wheat (X85228, Baga et al 1995) and tobacco (L02124, Diaz-De-Leon et al 1993) peroxidases.

A comparison of the promoter region, 1-1532 of SEQ ID NO:2, indicates that there are no similar sequences present within the GENBANK database.

Example 2

DNA Blot Analysis Using the Seed Coat Peroxidase cDNA Probe Reveals Restriction Fragment Length Polymorphisms Between EpEp and epep Genotypes Genomic DNA blots of OX347 (EpEp) and OX312 (epep) plants were hybridized with $^{32}$P-labelled cDNA to estimate the copy number of the seed coat peroxidase gene and to determine if this locus is polymorphic between the two genotypes. FIG. 4 shows the hybridization patterns after digestion with BamHI, XbaI, and SacI. Restriction fragment length polymorphisms are clearly visible in the BamHI and SacI digestions. The BamHI digestion produced a strongly hybridizing 17 kb fragment and a faint 3.4 kb fragment in the EpEp genotype. The 3.4 kb BamHI fragment is visible in the epep genotype but the 17 kb fragment has been replaced by a signal at >20 kb. The SacI digestion resulted in detection of three fragments in EpEp and epep plants. At least two fragments were expected here since the cDNA sequence has a SacI site within the open reading frame. However, the smallest and most strongly hybridizing of these fragments is 5.2 kb in EpEp plants and 4.9 kb in epep plants. Digestion with XbaI produced hybridizing fragments of ~14 kb and 7.8 kb for both genotypes, with the larger fragment showing a stronger signal.

Example 3

A Deletion Mutation Occurs in the Recessive ep Locus

Figure 5:
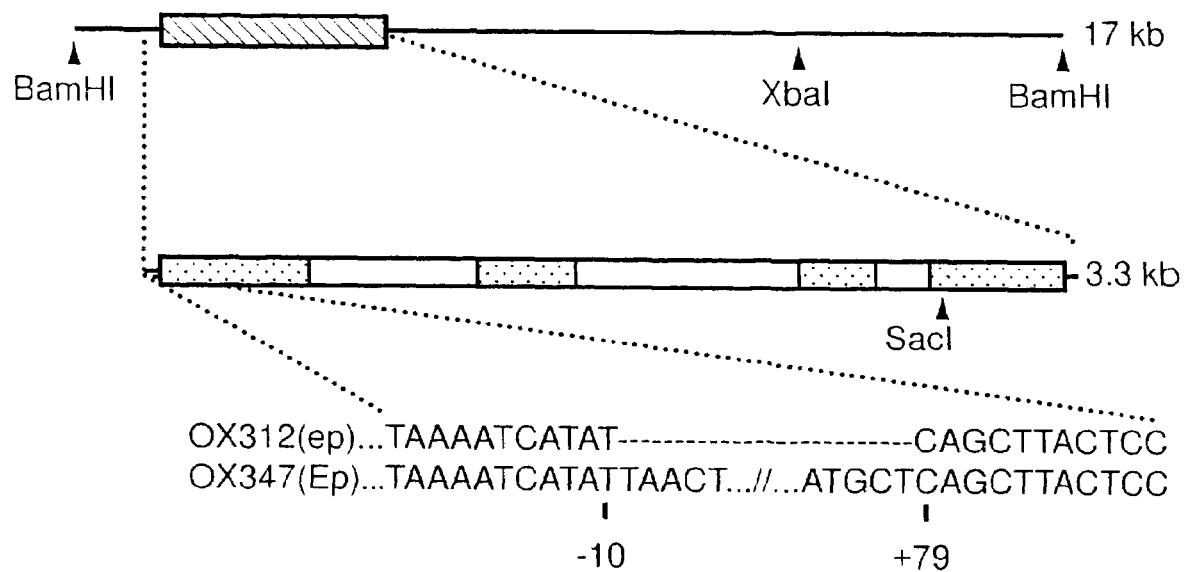
FIG. 5 exhibits the structure of the Ep Locus. A 17 kb fragment including the Ep locus is illustrated schematically. A 3.3 kb portion of the gene is enlarged and exons and introns are represented by shaded and open boxes, respectively. The final enlargement of the 5' region shows the location and DNA sequence around the 87 bp deletion occurring in the ep allele of soybean line OX312. Nucleotides are numbered by assigning +1 to the first base of the ATG start codon (OX347(Ep) sequence defined by nucleotides 1513-1621 of SEQ ID NO:2; OX342(ep) sequence defined by SEQ ID NO:20 (nucleotides 1513-1624 of SEQ ID NO:2 but with deletion of nucleotides 1524-1610).

The structural gene encoding the seed coat peroxidase is schematically illustrated in FIG. 5. The 17 kb BamHI fragment encompassing the gene includes 191 bp of sequence upstream from the translation start codon, three introns of 631 bp, 1030 bp, and 263 bp, and 13 kb of sequence downstream from the polyadenylation site. The arrangement of four exons and three introns and the placement of introns within the sequence is similar to that described for other plant peroxidases (Simon, 1992; Osakabe et al. 1995).

Figure 6:
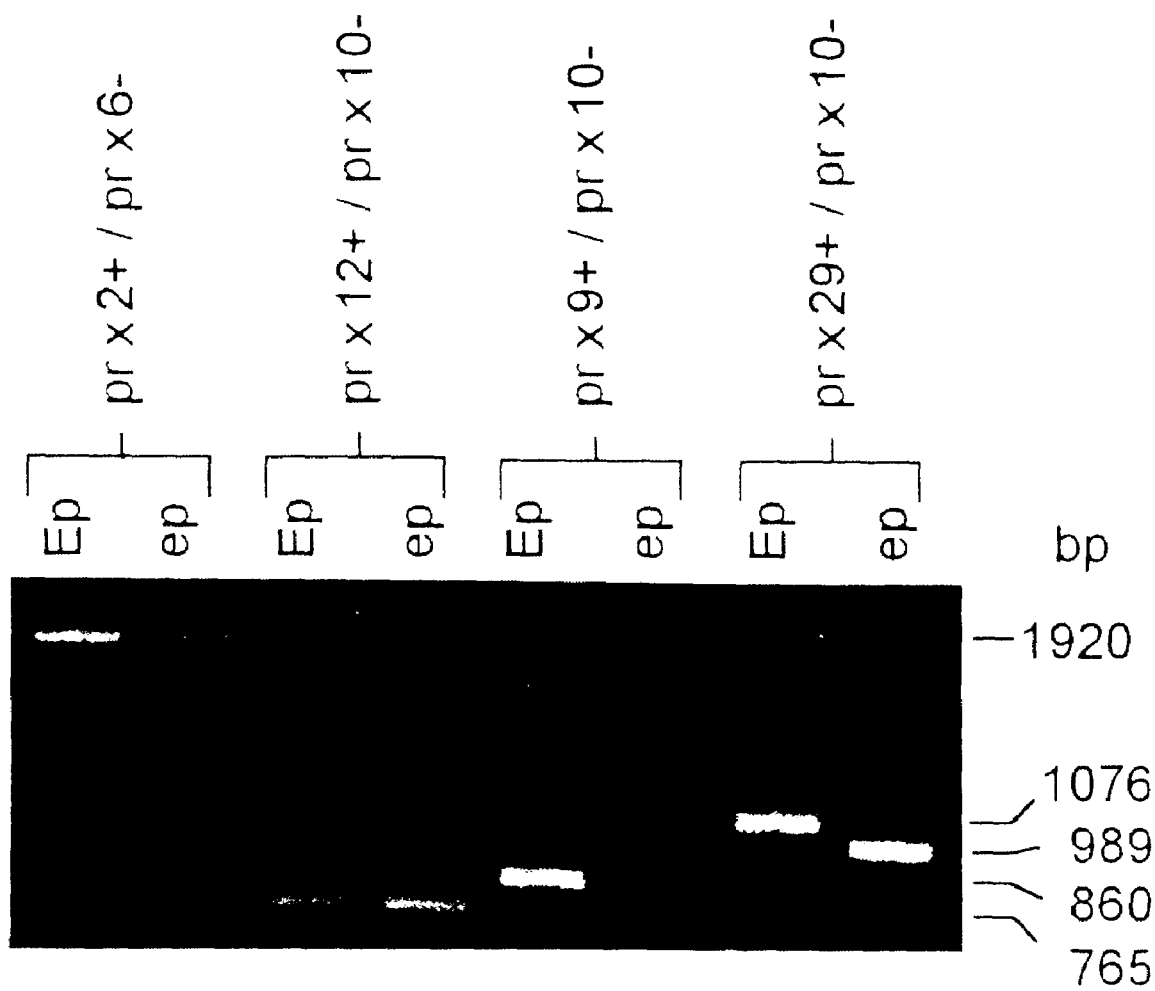
FIG. 6 displays PCR analysis of EpEp and epep genotypes using primers derived from the seed coat peroxidase cDNA. Genomic DNA from soybean lines OX312 (epep) and OX347 (EpEp) was used as template for PCR analysis with four different primer sets. Amplification products were separated by electrophoresis through a 0.8% agarose gel and visualized under UV light after staining with ethidium bromide. Genotype and primer combinations are indicated at the top of the figure. The size in base pairs of the amplified DNA fragments are indicated on the right.

Primers were designed from the DNA sequence to compare EpEp and epep genotypes by PCR analysis. FIG. 6 shows PCR amplification products from four different primer combinations using OX312 (epep) and OX347 (EpEp) genomic DNA as template. The primer annealing site for prx29+ begins 182 bp upstream from the ATG start codon; the remaining primer sites are shown in FIG. 1. Amplification with primers prx2+ and prx6−, and with prx12+ and prx10− produced the expected products of 1.9 kb and 860 bp, respectively, regardless of the Ep/ep genotype of the template DNA. However, PCR amplification with primers prx9+ and prx10−, and with prx29+ and prx10− generated the expected products only when template DNA was from plants carrying the dominant Ep allele. When template DNA was from an epep genotype, no product was detected using primers prx9+ and prx10− and a smaller product was amplified with primers prx29+ and prx10−. The products resulting from amplification of OX312 or OX347 template DNA with primers prx29+ and prx10− were directly sequenced and compared. The polymorphism is due to an 87 bp deletion occurring within this DNA fragment in OX312 plants, as shown in FIG. 5 (corresponding to nucleotides 1524 to 1610 of SEQ ID NO:2). This deletion begins nine bp upstream from the translation start codon and includes 78 bp of sequence at the 5' end of the open reading frame, including the prx9+ primer annealing site.

Figure 7A:
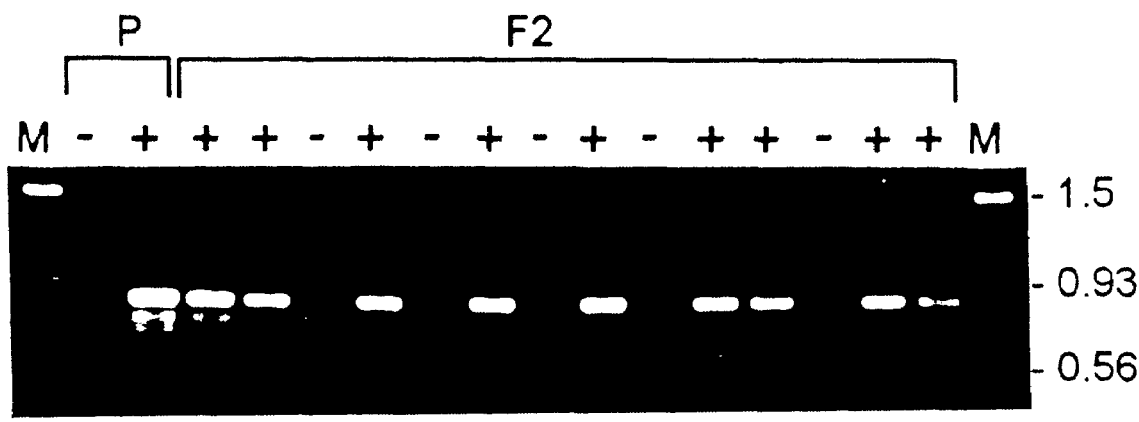
FIGS. 7A and 7B exhibit PCR analysis of an F2 population from a cross of EpEp and epep genotypes. Genomic DNA was used as template for PCR analysis of the parents (P) and 30 $F_2$ individuals. The cross was derived from the soybean lines OX312 (epep) and OX347 (EpEp). Plants were self pollinated and seeds were collected and scored for seed coat peroxidase activity. The symbols (−) and (+) indicate low and high seed coat peroxidase activity, respectively. Primers prx9+ and prx10− were used in the amplification reactions. Products were separated by electrophoresis through a 0.8% agarose gel and visualized under UV light after staining with ethidium bromide. The migration of molecular markers and their corresponding size in kb is also shown (lanes M).
Figure 7B:
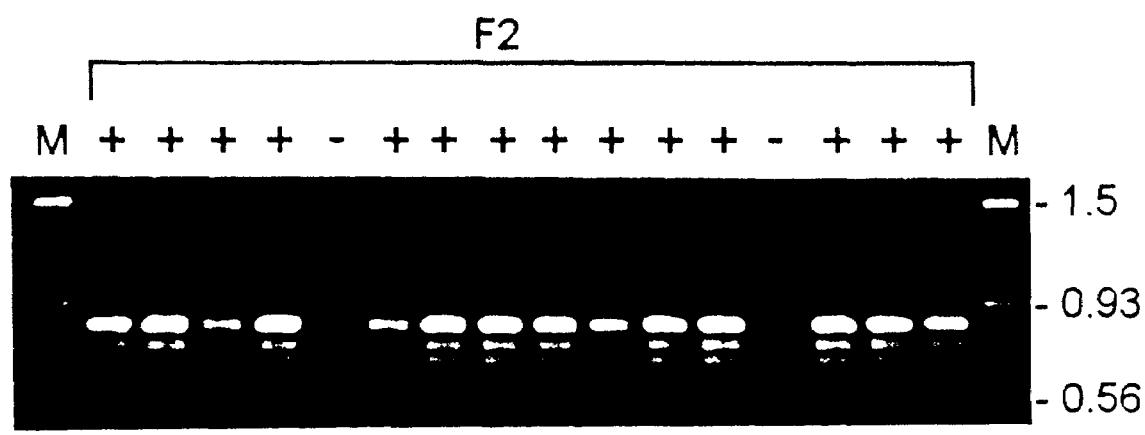

To test whether this deletion mutation cosegregates with the seed coat peroxidase phenotype, genomic DNA from an $F_2$ population segregating at the Ep locus was amplified using primers prx9+ and prx10− and $F_3$ seed was tested for seed coat peroxidase activity. FIG. 7 shows the results from this analysis. Of the 30 $F_2$ individuals tested, all 23 that were high in seed coat peroxidase activity produced the expected 860 bp PCR amplification product. The remaining seven $F_2$'s with low seed coat peroxidase activity produced no detectable PCR amplification products.

Figure 8A:
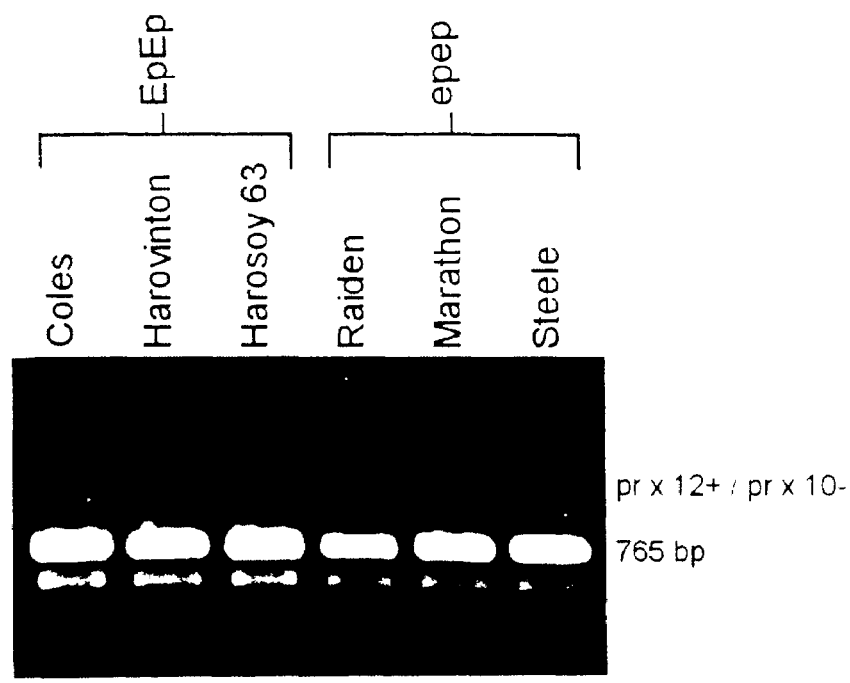
FIGS. 8A-8C display PCR analysis of six different soybean cultivars with primers derived from the seed coat peroxidase cDNA sequence. Genomic DNA was used as template for PCR analysis of three EpEp cultivars and three epep cultivars. Primers used in the amplification reactions and the size of the DNA product is indicated on the left. Products were separated by electrophoresis through a 0.8% agarose gel and visualized under UV light after staining with ethidium bromide.
Figure 8B:
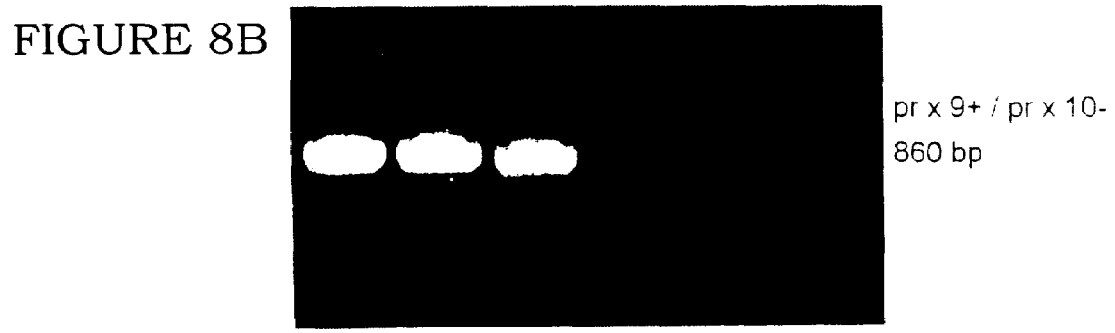
Figure 8C:
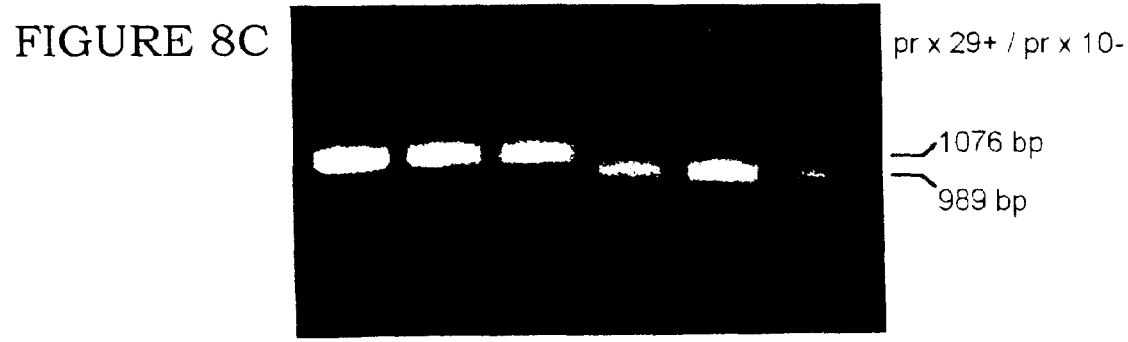

Finally, to determine if the OX312(epep) and OX347 (EpEp) breeding lines are representative of soybean cultivars that differ in seed coat peroxidase activity, several cultivars were tested by PCR analysis using primer combinations targeted to the Ep locus. FIG. 8 shows results from this analysis of six different soybean cultivars, three each of the homozygous dominant EpEp and recessive epep genotypes. As observed with OX312 and OX347, amplification products of the expected size were produced with primers prx12+ and prx10– regardless of the genotype, whereas epep genotypes yielded no product with primers prx9+ and prx10– or a smaller fragment with primers prx29+ and prx10–.

Example 4

Developmental Pattern of Expression of the Ep Gene

The seed coat peroxidase mRNA levels were determined by hybridizing RNA gel blots with radio labelled cDNA probe. FIG. 9 illustrates the transcript abundance in various tissues of epep and EpEp plants. The mRNA accumulated to high levels in seed coat tissues of EpEp plants, especially in the later stages development when whole seed fresh weight exceeded 50 mg. Low levels of transcript could also be detected in root tissues but not in the flower, embryo, pod or leaf. The transcript could also be detected in seed coat and root tissues epep plants bu in drastically reduced amounts compared to the EpEp genotype. The reduced amounts of peroxidase mRNA present in seed coats of epep plants indicates that the transcriptional process and/or the stability of the resulting mRNA is severely affected. The Ep gene has a TATA box and a 5' cap signal beginning 47 bp and 15 bp, respectively, upstream from the translation start codon. The 87 bp deletion in the ep allele extends into the 5' cap signal and therefore could interfere with transcript processing. Regardless, any resulting transcript will not be properly translated since the AUG initiation codon and the entire amino-terminal signal sequence is deleted from the ep allele. Not wishing to be bound by theory, the lack of peroxidase accumulation in seed coats of epep plants appears to be due to at least two factors, greatly reduced transcript levels and ineffective translation, resulting from mutation of the structural gene encoding the enzyme. In summary, the results indicate that the Ep gene regulatory elements can drive high level expression in a tightly coordinate, tissue and developmentally specific manner.

All scientific publications and patent documents are incorporated herein by reference.

The present invention has been described with regard to preferred embodiments. However, it will be obvious to persons skilled in the art that a number of variations and modifications can be made without departing from the scope of the invention as described in the following claims.

REFERENCES

Abrahams, S. L., Hayes, C. M., and Watson, J. M. (1994) Organ-specific expression of three peroxidase-encoding cDNAs from lucerne (*Medicago sativa*). GenBank Accession # L36156.

Baga, M. Chibbar, R. N., and Kartha, K. K., (1995) Molecular cloning and expression analysis of peroxidase genes from wheat. *Plant Molec. Biol.* 29, 647-662

Baker, D. M., Minor, H. C., and Cumbie, B. G. (1987) Scanning electron microscopy examination of soybean testa development. *Can. J. Bot.* 65, 2420-2424.

Bowles, D. J. (1990) Defense-related proteins in higher plants. *Annu. Rev. Biochem.* 59, 873-907.

Buttery, B. R., and Buzzell, R. I. (1968) Peroxidase activity in the seeds of soybean varieties. *Crop Sci.* 8, 722-725.

Buzzell, R. I., and Buttery, B. R. (1969) Inheritance of peroxidase activity in soybean seed coats. *Crop Sci.* 9, 387-388.

Campa, A. (1991) Biological roles of plant peroxidases: known and potential function. In *Peroxidases in Chemistry and Biology*, Volume II (J. Everse, K. E. Everse and M. B. Grisham, eds). Boca Raton, Fla.: CRC Press, pp. 25-50.

Dellaporta, S. L., Wood, J., and Hicks, J. B. (1983) A plant DNA minipreparation. Version II. *Plant Mol. Biol. Rep.* 1, 19-21.

Diaz-De-Leon, f., Klotz, K. L., and Lagrimini, M. (1993) Nucleotide Sequence of the Tobacco (*Nicotiana tabacum*) anionic peroxidase gene. *Plant Physiol.* 101, 1117-1118.

el-Turk, J., Asemota, O., Leymarie, J., Sallaud, C., Mesnage, S., Breda, C., Buffard, D., Kondorosi, A., and Esnault, R. (1996) Nucleotide sequence of four pathogen-induced alfalfa peroxide-encoding cDNAs. *Gene* 170, 213-216.

Freiberg B., (1995) Indiana Crop: Keeping Its Members Up with the Changing Times. *Seed Crops Indust*. March, 4-9

Fujiyama, K., Takemura, H., Shibayama, S., Kobayashi, K., Choi, J.-K., Shinmyo, A., Takano, M., Yamada, Y, and Okada, H. (1988) Structure for the Horseradish Peroxidase isozyme c genes. *Eur. J. Biochem.* 173, 681-687.

Geierson and Corey (1988), *Plant Molecular Biology*, 2d Ed.

Gijzen, M., van Huystee, R., and Buzzell, R. I. (1993) Soybean seed coat peroxidase. A comparison of high-activity and low-activity genotypes. *Plant Physiol.* 103, 1061-1066.

Gillikin, J. W., and Graham, J. S. (1991) Purification and developmental analysis of the major anionic peroxidase from the seed coat of soybean. *Plant Physiol.* 96, 214-220.

Gray, J. S. S., Yang, B. Y., Hull, S. R., Venzke, D. P., and Montgomery, R. (1996) The glycans of soybean peroxidase. *Glycobiology* 6, 23-32.

Lagrimini, M. L., Bradford., and Rothstein S, (1990) Peroxidase-Induced Wilting in Transgenic Tobacco. *Plant Cell* 2, 7-18.

McEldoon, J. P., Pokora A. R., and Dordick, J. S. (1995) Lignin peroxidase-type activity of soybean peroxidase. *Enzyme Microb. Technol.* 17, 359-365.

Moerschbacher, B. M. (1992) Plant peroxidases: involvement in response to pathogens. In *Plant Peroxidases 1980-1990: Topics and Detailed Literature on Molecular, Biochemical, and Physiological Aspects*, (C. Penel, T. Gaspar and H. Greppin, eds). Geneva: University of Geneva, pp. 91-115.

Omann, F., and Tyson, H., (1995) cDNA sequence of a peroxidase from flax (*Linum usitissimum*), GenBank Accession # L07554.

Osakabe, K., Koyama, H., Kawai, S., Katayama, Y., and Morohoshi, N. (1993) Nucleotide sequence for the genomic DNA encoding the anionic peroxidase gene from *Nicotiana tabacum*. GenBank Accession # D11396.

Osakabe, K., Koyama, H., Kawai, S., Katayama, Y., and Morohoshi, N. (1994)

Molecular cloning and nucleotide sequences of two novel cDNA that encode anionic peroxidases of *Populas kitakamiensis*. GenBank Accession # D30652.

Osakabe, K., Koyama, H., Kawai, S., Katayama, Y., and Morohoshi, N. (1995) Molecular cloning of two tandemly arranged peroxidase genes from *Populus kitakamiensis* and their differential regulation in the stem. *Plant Mol. Biol.* 28, 677-689.

Rasmussen, J. B., Smith, J. A., Williams, S., Burkhart, W., Ward, E. R., Somerville, S. C., Ryals, J., and Hammerschmidt, R. (1992) Cloning and Systemic Expression of an acidic peroxidase associated with systemic acquired resistance to disease in cucumber. GenBank Accession # M91373.

Sambrook, J., Fritsch, E. F., and Maniatis, T. (1989) *Molecular Cloning: A Laboratory Manual*, 2nd Edn. Cold Spring Harbor, N.Y.: Cold Spring Harbor Laboratory Press.

Schuller, D. J., Ban, N., van Huystee, R. B., McPherson, A., and Poulos, T. L. (1996) The crystal structure of peanut peroxidase. *Structure* 4, 311-321.

Scott-Craig, J. S., Kerby, K. B., Stein, B. D, and Sommerville, S. C. (1994) Expression of an extracellular peroxidase that is induced in barley (*Hordeum vulgare*) by the powdery mildew pathogen (*Erysiphe graminis* f. sp. *hordei*). GenBank Accession # L36093.

Sessa, D. J., and Anderson, R. L. (1981) Soybean peroxidases: Purification and some properties. *J. Agric. Food Chem.* 29, 960-965.

Simon, P. (1992) Molecular cloning of plant peroxidases. In *Plant Peroxidases 1980-1990: Topics and Detailed Literature on Molecular, Biochemical, and Physiological Aspects* (C. Penel, T. Gaspar and H. Greppin, eds) Geneva: University of Geneva, pp. 47-58.

Wang, C. S., and Vodkin, L. O. (1994) Extraction of RNA from tissues containing high levels of procyanidins that bind RNA. *Plant Mol. Biol. Rep.* 12, 132-145.

Weissbach and Weissbach, (1988) *Methods for Plant Molecular Biology*, Academy Press, New York VIII, pp. 421-463

Wick, C. B. (1995) Enzymol International Shows Promise of Novel Peroxidase, *Chem. Eng. News*, pp. 1

Welinder, K. G. (1992) Plant peroxidase structure-function relationships. In *Plant Peroxidases 1980-1990: Topics and Detailed Literature on Molecular, Biochemical, and Physiological Aspects* (C. Penel, T. Gaspar and H. Greppin, eds) Geneva: University of Geneva, pp. 1-24.

The invention claimed is:

1. An isolated DNA molecule comprising the nucleotide sequence of SEQ ID NO:1.

2. A vector which comprises the DNA molecule of claim 1.

3. A transgenic host cell expressing the DNA molecule within the vector of claim 2.

4. A transgenic plant comprising the vector of claim 2.

5. An isolated DNA molecule comprising the nucleotide sequence of nucleotides 1-1532 or nucleotides 1533-4700 of SEQ ID NO:2.

6. The isolated DNA molecule of claim 5 comprising the nucleotide sequence of nucleotides 1-4700 of SEQ ID NO:2.

7. The isolated DNA molecule of claim 5, comprising the nucleotide sequence of nucleotides 1-1532 of SEQ ID NO:2.

8. The isolated DNA molecule of claim 5 comprising nucleotides 1533-4700 of SEQ ID NO:2.

9. A vector which comprises the DNA molecule of claim 5.

10. A transgenic host cell expressing the DNA molecule within the vector of claim 9.

11. A transgenic plant comprising the vector of claim 9.

12. An isolated DNA molecule comprising a nucleotide sequence that hybridizes to nucleotides 1-1532 of SEQ ID NO:2 or a complement thereof, wherein hybridization conditions comprise hybridisation in 6×SSC, 20 mM $Na_2HPO_4$, 0.4% SDS, 500 µg/ml Salmon sperm DNA at 65° C. for 20 hours, followed by a wash with 2×SSC, 0.5% SDS at 20° C., and a wash at 65° C. with 0.1×SSC, 0.5% SDS, wherein the nucleotide sequence is a promoter.

13. A vector comprising the DNA molecule of claim 12.

14. The vector of claim 13 which comprises a heterologous gene of interest under control of the DNA molecule.

15. A transgenic seed coat cell expressing the DNA molecule within the vector of claim 14.

16. A transgenic soybean plant comprising the vector of claim 14.

17. A transgenic seed coat cell expressing a gene of interest under control of a regulatory region, wherein the gene of interest and regulatory region are contained within the vector of claim 13.

18. A transgenic soybean plant comprising the vector of claim 13.

19. An isolated DNA molecule comprising a nucleotide sequence selected from the group consisting of nucleotides 1752-2382, nucleotides 2575-3604, and nucleotides 3770-4032 of SEQ ID NO:2.

20. The isolated DNA molecule of claim 19 comprising nucleotides 2575-3604 of SEQ ID NO:2.

21. The isolated DNA molecule of claim 19 comprising nucleotides 3770-4032 of SEQ ID NO:2.

22. A method for the production of soybean seed coat peroxidase in a host comprising:
   i) transforming the host with a vector comprising the isolated DNA molecule as defined in claim 1 operably linked with a regulatory region; and
   ii) culturing the host under conditions to allow expression of the soybean seed coat peroxidase.

23. A process for producing a heterologous gene of interest in a transgenic soybean plant comprising, transforming the transgenic soybean plant with the heterologous gene of interest under control of a regulatory region, the heterologous gene of interest and the regulatory region contained within the vector of claim 13, and growing the transgenic plant under conditions to allow expression of the heterologous gene of interest.

24. The process of claim 23 wherein the heterologous gene of interest is produced within seed coat cells.

25. A method of selecting between an EpEp and an epep plant genotype comprising the steps of:
   a) preparing genomic DNA, or cDNA from a plant;
   b) fragmenting the genomic DNA or cDNA to produce DNA fragments;
   c) amplifying the DNA fragments using at least one primer, the at least one primer comprises 20 contiguous nucleotides selected from nucleotides 1524-1610 of SEQ ID NO:2, to produce an amplified product; and
   e) determining whether the amplified product is representative of an EpEp or an epep genotype.

26. A method of selecting a soybean plant having a deletion in a peroxidase gene, which method comprises the steps of:
   a) preparing genomic DNA, or cDNA from a plant;
   b) fragmenting the genomic DNA or cDNA to produce DNA fragments;
   c) amplifying the DNA fragments using at least one primer, the at least one primer comprises 20 contiguous nucleotides selected from nucleotides 1524-1610 of SEQ ID NO:2, to produce an amplified product; and
   e) determining whether the amplified product is representative of an EpEp genotype or a genotype of a soybean plant having a deletion in a peroxidase gene.

27. The isolated DNA molecule of claim 19 comprising nucleotides 1752-2382 of SEQ ID NO:2.

28. An isolated DNA molecule comprising a nucleotide sequence that hybridizes to the complement of nucleotides 1-1532 of SEQ ID NO:2, wherein hybridization conditions comprise hybridisation in 6×SSC, 20 mM $Na_2HPO_4$, 0.4% SDS, 500 μg/ml Salmon sperm DNA at 65° C. for 20 hours, followed by a wash with 2×SSC, 0.5% SDS at 20° C., and a wash at 65° C. with 0.1×SSC, 0.5% SDS, wherein the nucleotide sequence is a promoter.

29. A vector comprising the DNA molecule of claim 28.

30. The vector of claim 29 which comprises a heterologous gene of interest under control of the DNA molecule.

31. A transgenic seed coat cell expressing the DNA molecule within the vector of claim 30.

32. A transgenic soybean plant comprising the vector of claim 30.

33. A transgenic seed coat cell expressing a gene of interest under control of a regulatory region, wherein the gene of interest and regulatory region are contained within the vector of claim 29.

34. A transgenic soybean plant comprising the vector of claim 29.

35. A process for producing a heterologous gene of interest in a transgenic soybean plant comprising, transforming the transgenic soybean plant with the heterologous gene of interest under control of a regulatory region, the heterologous gene of interest and the regulatory region contained within the vector of claim 29, and growing the transgenic plant under conditions to allow expression of the heterologous gene of interest.

36. The process of claim 35 wherein the heterologous gene of interest is produced within seed coat cells.

* * * * *

SEQUENCE LISTING

```
<160> NUMBER OF SEQ ID NOS: 20

<210> SEQ ID NO 1
<211> LENGTH: 1244
<212> TYPE: DNA
<213> ORGANISM: Glycine max
<220> FEATURE:
<221> NAME/KEY: CDS
<222> LOCATION: (1)..(1056)
<221> NAME/KEY: sig_peptide
<222> LOCATION: (1)..(78)

<400> SEQUENCE: 1 atg ggt tcc atg cgt cta tta gta gtg gca ttg ttg tgt gca ttt gct      48
Met Gly Ser Met Arg Leu Leu Val Val Ala Leu Leu Cys Ala Phe Ala
1               5                   10                  15 atg cat gca ggt ttt tca gtc tct tat gct cag ctt act cct acg ttc      96
Met His Ala Gly Phe Ser Val Ser Tyr Ala Gln Leu Thr Pro Thr Phe
                20                  25                  30 tac aga gaa aca tgt cca aat ctg ttc cct att gtg ttt gga gta atc     144
Tyr Arg Glu Thr Cys Pro Asn Leu Phe Pro Ile Val Phe Gly Val Ile
            35                  40                  45 ttc gat gct tct ttc acc gat ccc cga atc ggg gcc agt ctc atg agg     192
Phe Asp Ala Ser Phe Thr Asp Pro Arg Ile Gly Ala Ser Leu Met Arg
        50                  55                  60 ctt cat ttt cat gat tgc ttt gtt caa ggt tgt gat gga tca gtt ttg     240
Leu His Phe His Asp Cys Phe Val Gln Gly Cys Asp Gly Ser Val Leu
65                  70                  75                  80 ctg aac aac act gat aca ata gaa agc gag caa gat gca ctt cca aat     288
Leu Asn Asn Thr Asp Thr Ile Glu Ser Glu Gln Asp Ala Leu Pro Asn
                85                  90                  95 atc aac tca ata aga gga ttg gac gtt gtc aat gac atc aag aca gcg     336
Ile Asn Ser Ile Arg Gly Leu Asp Val Val Asn Asp Ile Lys Thr Ala
            100                 105                 110 gtg gaa aat agt tgt cca gac aca gtt tct tgt gct gat att ctt gct     384
Val Glu Asn Ser Cys Pro Asp Thr Val Ser Cys Ala Asp Ile Leu Ala
        115                 120                 125
```

```
att gca gct gaa ata gct tct gtt ctg gga gga ggt cca gga tgg cca      432
Ile Ala Ala Glu Ile Ala Ser Val Leu Gly Gly Gly Pro Gly Trp Pro
        130                 135                 140 gtt cca tta gga aga agg gac agc tta aca gca aac cga acc ctt gca      480
Val Pro Leu Gly Arg Arg Asp Ser Leu Thr Ala Asn Arg Thr Leu Ala
145                 150                 155                 160 aat caa aac ctt cca gca cct ttc ttc aac ctc act caa ctt aaa gct      528
Asn Gln Asn Leu Pro Ala Pro Phe Phe Asn Leu Thr Gln Leu Lys Ala
                165                 170                 175 tcc ttt gct gtt caa ggt ctc aac acc ctt gat tta gtt aca ctc tca      576
Ser Phe Ala Val Gln Gly Leu Asn Thr Leu Asp Leu Val Thr Leu Ser
            180                 185                 190 ggt ggt cat acg ttt gga aga gct cgg tgc agt aca ttc ata aac cga      624
Gly Gly His Thr Phe Gly Arg Ala Arg Cys Ser Thr Phe Ile Asn Arg
        195                 200                 205 tta tac aac ttc agc aac act gga aac cct gat cca act ctg aac aca      672
Leu Tyr Asn Phe Ser Asn Thr Gly Asn Pro Asp Pro Thr Leu Asn Thr
    210                 215                 220 aca tac tta gaa gta ttg cgt gca aga tgc ccc cag aat gca act ggg      720
Thr Tyr Leu Glu Val Leu Arg Ala Arg Cys Pro Gln Asn Ala Thr Gly
225                 230                 235                 240 gat aac ctc acc aat ttg gac ctg agc aca cct gat caa ttt gac aac      768
Asp Asn Leu Thr Asn Leu Asp Leu Ser Thr Pro Asp Gln Phe Asp Asn
                245                 250                 255 aga tac tac tcc aat ctt ctg cag ctc aat ggc tta ctt cag agt gac      816
Arg Tyr Tyr Ser Asn Leu Leu Gln Leu Asn Gly Leu Leu Gln Ser Asp
            260                 265                 270 caa gaa ctt ttc tcc act cct ggt gct gat acc att ccc att gtc aat      864
Gln Glu Leu Phe Ser Thr Pro Gly Ala Asp Thr Ile Pro Ile Val Asn
        275                 280                 285 agc ttc agc agt aac cag aat act ttc ttt tcc aac ttt aga gtt tca      912
Ser Phe Ser Ser Asn Gln Asn Thr Phe Phe Ser Asn Phe Arg Val Ser
    290                 295                 300 atg ata aaa atg ggt aat att gga gtg ctg act ggg gat gaa gga gaa      960
Met Ile Lys Met Gly Asn Ile Gly Val Leu Thr Gly Asp Glu Gly Glu
305                 310                 315                 320 att cgc ttg caa tgt aat ttt gtg aat gga gac tcg ttt gga tta gct     1008
Ile Arg Leu Gln Cys Asn Phe Val Asn Gly Asp Ser Phe Gly Leu Ala
                325                 330                 335 agt gtg gcg tcc aaa gat gct aaa caa aag ctt gtt gct caa tct aaa     1056
Ser Val Ala Ser Lys Asp Ala Lys Gln Lys Leu Val Ala Gln Ser Lys
            340                 345                 350 taaaccaata attaatgggg atgtgcatgc tagctagcat gtaaaggcaa attaggttgt     1116
aaacctcttt gctagctata ttgaaataaa ccaaggagt agtgtgcatg tcaattcgat      1176
tttgccatgt acctcttgga atattatgta ataattattt gaatctcttt aaggtactta     1236
attaatca                                                              1244

<210> SEQ ID NO 2
<211> LENGTH: 4700
<212> TYPE: DNA
<213> ORGANISM: Glycine max
<220> FEATURE:
<221> NAME/KEY: promoter
<222> LOCATION: (1)..(1532)
<221> NAME/KEY: sig_peptide
<222> LOCATION: (1533)..(1610)
<221> NAME/KEY: exon
<222> LOCATION: (1533)..(1751)
<221> NAME/KEY: exon
<222> LOCATION: (2383)..(2574)
<221> NAME/KEY: exon
```

-continued

```
<222> LOCATION: (3605)..(3769)
<221> NAME/KEY: exon
<222> LOCATION: (4033)..(4515)
<221> NAME/KEY: Intron
<222> LOCATION: (1752)..(2382)
<221> NAME/KEY: Intron
<222> LOCATION: (2575)..(3604)
<221> NAME/KEY: Intron
<222> LOCATION: (3770)..(4032)
<221> NAME/KEY: CDS
<222> LOCATION: (1533)..(1751)
<221> NAME/KEY: CDS
<222> LOCATION: (2383)..(2574)
<221> NAME/KEY: CDS
<222> LOCATION: (3605)..(3769)
<221> NAME/KEY: CDS
<222> LOCATION: (4033)..(4512)

<400> SEQUENCE: 2
tagataaaaa aatgggatat aattttttctc agatgttgtt tatactgttt ttttaatcag     60
aattaaaatt cctctttaat tatcgacata atttttttg gtgaatatta tcgacataat     120
tatttaatac aaattttat tgtacataga agtgatactt caattttaat attggagaac      180
agtacgaaaa cataaaaaaa ctgttattag aagaaaaaaa tatatggaaa aggttagcta     240
catatattag ctaaattagt tgttctaatt ggctatataa accctattgt actctttgta     300
atctcacctt tttcatttaa atacatttct acttttaag ttctatattt tctctcaatt      360
ttcttcgata aaccatgaaa tttaacatgg tatatcagcg ataccaccca ctttgaaagc     420
catgtatggc tagtatgggc agccaaaatt tgccctggtt caagcaaagc aagtgtttat     480
atagatgtga cttttgttga ggaactcatg ccaatggtac tgattgtgaa actgagaaaa     540
ctaatttgga gaattgaat tatgatcatt aaatactcct ctcctgacta ccttcgtccc      600
tcaaatttgt accatcatta tttcccaaaa atttgattac aatgcactaa ttaatgaatg     660
tttcttacat tatcatatta tcatatctga cattttgttt ttacttttta taataattat     720
tttaaaaagt catacatgca aataattttt taatagttta cagttaaatt tttacagtaa     780
aaatgcatga aaattaaact ttattttcc aagtcatcat ttagtcaaat cccaaaacaa      840
tgattatttt ttgcaaatga atgtttattg aacatttaaa tgtagcctaa ttaattctgg     900
ttatggtgtc aatgttccaa aacctaatgc aagatcttag caagtacata catagatcta     960
attttaaact tatcttacg caagagatat aaagattata catctagttt taaacattaa     1020
cttttgtttt tgtgttaaaa aacagtaaca ttttcttaat tttgtagagt gacgtgctcc     1080
aaccatatta acgaagattt taattggtat tcaagttcat gaacttagta aataagtttt     1140
ggtcttcagt tttcaatttt cattacaaca tttatgtaaa atatcaacgt tttctgaaat     1200
ttgttgcttg tgtgctccaa ccacatttaa gagattatag aaattaattt tcaagaagat     1260
aatgattcct actcttgctg gccctaccat agtacaataa atccactcat aaatcaacaa     1320
gtcgtcgtca taggcaattg ggcatcatat cataaacaat acgtacgtga tattatctag     1380
tgtctctcag tttactttat gagaaattat ttttctttaa aaaagttaa ttaataaaaa      1440 catttgcgat accgtgagtt acaagaaatc cgccgaattc atctctataa ataaaaggat     1500
ctatatgaga ggtaaaatca tattaactca aa atg ggt tcc atg cgt cta tta      1553
                                   Met Gly Ser Met Arg Leu Leu
                                    1               5 gta gtg gca ttg ttg tgt gca ttt gct atg cat gca ggt ttt tca gtc     1601
Val Val Ala Leu Leu Cys Ala Phe Ala Met His Ala Gly Phe Ser Val
         10                  15                  20 tct tat gct cag ctt act cct acg ttc tac aga gaa aca tgt cca aat     1649
```

-continued

```
Ser Tyr Ala Gln Leu Thr Pro Thr Phe Tyr Arg Glu Thr Cys Pro Asn
    25                  30                  35 ctg ttc cct att gtg ttt gga gta atc ttc gat gct tct ttc acc gat     1697
Leu Phe Pro Ile Val Phe Gly Val Ile Phe Asp Ala Ser Phe Thr Asp
 40                  45                  50                  55 ccc cga atc ggg gcc agt ctc atg agg ctt cat ttt cat gat tgc ttt     1745
Pro Arg Ile Gly Ala Ser Leu Met Arg Leu His Phe His Asp Cys Phe
                 60                  65                  70 gtt caa gtacgtactt ttttttttcc ttccaaaatg ccctgcatat ttaacaagat       1801
Val Gln tgctttgttc acctagaaaa atgtgttttt ttcaacgatc ttacgtacgt ttgtttggtt    1861 tgaaaataa atcagaaaga gatcaagaaa atagctagaa agaaagcaac gtttttttaa     1921
aaggtattta gtgtgagaaa atattaaaa ctgaagagaa agaaattaaa taagcttttc     1981
ttgaatgata tttacatgtc ttattaactt aaagtcacct tttttcttta agttgtgctt    2041
gaagaaaaaa gatgtctttc agtttagttt tgattaatgc taattatatt tttaattaat    2101
taattaatac tatatatcta tttaccatat taattattac tatatttcat gatgacaaca    2161
gacaagtatt ctaaagaggt atcggtagat gattaattttt tttataaaaa atcttttgc    2221 gtgtatagat attctttat aattggtgca gaaacttgta atgctaattg caattaatct     2281
tacattgatt aactaatagc tataatcaat atttaggtta ggtataggag acaaatcaag    2341
tgatctgaac aaattaagtt gttatatttg cattgtgaca g ggt tgt gat gga tca   2397
                                             Gly Cys Asp Gly Ser
                                                            75 gtt ttg ctg aac aac act gat aca ata gaa agc gag caa gat gca ctt     2445
Val Leu Leu Asn Asn Thr Asp Thr Ile Glu Ser Glu Gln Asp Ala Leu
 80                  85                  90 cca aat atc aac tca ata aga gga ttg gac gtt gtc aat gac atc aag     2493
Pro Asn Ile Asn Ser Ile Arg Gly Leu Asp Val Val Asn Asp Ile Lys
 95                 100                 105                 110 aca gcg gtg gaa aat agt tgt cca gac aca gtt tct tgt gct gat att     2541
Thr Ala Val Glu Asn Ser Cys Pro Asp Thr Val Ser Cys Ala Asp Ile
                115                 120                 125 ctt gct att gca gct gaa ata gct tct gtt ctg gtaattaata actcctaatt   2594
Leu Ala Ile Ala Ala Glu Ile Ala Ser Val Leu
            130                 135 aattcccaac cattaaaaag ttgcatgatt ggattcaaaa ttctatggta ttggggttct    2654
gatataaatt tgtaattaaa ttgcactaaa aaaattatc atatactttt aataaaaaaa    2714
atttatctaa tttaattat tattaaaact attttaaaa ttcaatccta actctttttt     2774
aatcggagca tgtaagctgg cacccaccgt atatcgttgg aagatgctat aaaaccattt   2834
aattaatgga tggaatcagt caaaacattt aattcaaaat actcttaatt gtgattagta   2894
atcatgttcg ggcaagttac gttgtgtata attaatttga cttaatcaga taaaaaaaca   2954
aatggacgca agccggttgg tatagatatc actggcctgt agaatatgtg gttttttcacg  3014 tttaaataaa agctagctac tatattatat ttagtctttt ttttttcttaa acccatttaa  3074 cgtgatttat tgactgtgaa acatgttttcc acacacaggc ttagaaactc ctcgcaacta  3134
acatctccaa aatttgacta tttatttatg aagataattc atctatgatg ttcaactcta  3194
ttatatatat gtatcatcgc agtattaaga attataatag tcaaatatag aagtatatcg   3254
ggtaaatgta gttgcatgtg cgacctgttt cgtgtaaaat gcttattcta tatagctttt   3314
tttattggaa aataacgatg aactaaaaac gaaagggtat catatagttt gactttatg    3374 ttagagagag acatcttaat ttggtcatat gttaaataat taattacaat gcatacacaa   3434
```

```
                                                       -continued atatttatgc catatctaaa aaatgataaa atatcatagg tatactcaac tatatgatat  3494
ccccataaca gaaattgtac ttttcttcag gcaatgaact taacatttct gtttgctaaa  3554
aacaaacatc cacttaaagt ggttcaacat atttatgtaa taatttacag gga gga     3610
                                                          Gly Gly ggt cca gga tgg cca gtt cca tta gga aga agg gac agc tta aca gca   3658
Gly Pro Gly Trp Pro Val Pro Leu Gly Arg Arg Asp Ser Leu Thr Ala
140             145                 150                 155 aac cga acc ctt gca aat caa aac ctt cca gca cct ttc ttc aac ctc   3706
Asn Arg Thr Leu Ala Asn Gln Asn Leu Pro Ala Pro Phe Phe Asn Leu
                160                 165                 170 act caa ctt aaa gct tcc ttt gct gtt caa ggt ctc aac acc ctt gat   3754
Thr Gln Leu Lys Ala Ser Phe Ala Val Gln Gly Leu Asn Thr Leu Asp
            175                 180                 185 tta gtt aca ctc tca ggtatacata atcaattttt tatttgctat tagctagcaa   3809
Leu Val Thr Leu Ser
            190 taaaaagtct ctgatacaga catatttaga taaattaatt tctccataaa catttataat  3869 aaaattatca atttatgtac ttaaaaatta tggattgaag ctcttttcat ccaactttta  3929 ctaaagttaa ggtgcatata ataaaaata aactatctct tgtttcttat aaaaagattg  3989 aagataagtt aaagtctact tataaatcat taatatatgt ata ggt ggt cat acg  4044
                                                Gly Gly His Thr
                                                        195 ttt gga aga gct cgg tgc agt aca ttc ata aac cga tta tac aac ttc   4092
Phe Gly Arg Ala Arg Cys Ser Thr Phe Ile Asn Arg Leu Tyr Asn Phe
            200                 205                 210 agc aac act gga aac cct gat cca act ctg aac aca aca tac tta gaa   4140
Ser Asn Thr Gly Asn Pro Asp Pro Thr Leu Asn Thr Thr Tyr Leu Glu
        215                 220                 225 gta ttg cgt gca aga tgc ccc cag aat gca act ggg gat aac ctc acc   4188
Val Leu Arg Ala Arg Cys Pro Gln Asn Ala Thr Gly Asp Asn Leu Thr
    230                 235                 240 aat ttg gac ctg agc aca cct gat caa ttt gac aac aga tac tac tcc   4236
Asn Leu Asp Leu Ser Thr Pro Asp Gln Phe Asp Asn Arg Tyr Tyr Ser
245                 250                 255                 260 aat ctt ctg cag ctc aat ggc tta ctt cag agt gac caa gaa ctt ttc   4284
Asn Leu Leu Gln Leu Asn Gly Leu Leu Gln Ser Asp Gln Glu Leu Phe
                265                 270                 275 tcc act cct ggt gct gat acc att ccc att gtc aat agc ttc agc agt   4332
Ser Thr Pro Gly Ala Asp Thr Ile Pro Ile Val Asn Ser Phe Ser Ser
            280                 285                 290 aac cag aat act ttc ttt tcc aac ttt aga gtt tca atg ata aaa atg   4380
Asn Gln Asn Thr Phe Phe Ser Asn Phe Arg Val Ser Met Ile Lys Met
        295                 300                 305 ggt aat att gga gtg ctg act ggg gat gaa gga gaa att cgc ttg caa   4428
Gly Asn Ile Gly Val Leu Thr Gly Asp Glu Gly Glu Ile Arg Leu Gln
    310                 315                 320 tgt aat ttt gtg aat gga gac tcg ttt gga tta gct agt gtg gcg tcc   4476
Cys Asn Phe Val Asn Gly Asp Ser Phe Gly Leu Ala Ser Val Ala Ser
325                 330                 335                 340 aaa gat gct aaa caa aag ctt gtt gct caa tct aaa taa accaataatt   4525
Lys Asp Ala Lys Gln Lys Leu Val Ala Gln Ser Lys
                345                 350 aatggggatg tgcatgctag ctagcatgta aaggcaaatt aggttgtaaa cctctttgct  4585
agctatattg aaataaacca aaggagtagt gtgcatgtca attcgatttt gccatgtacc  4645
tcttggaata ttatgtaata attatttgaa ctctctttaag gtacttaatt aatca      4700
```

<210> SEQ ID NO 3
<211> LENGTH: 17
<212> TYPE: DNA
<213> ORGANISM: degenerate probe

<400> SEQUENCE: 3
ttycaygayt gyttygt                                                  17

<210> SEQ ID NO 4
<211> LENGTH: 20
<212> TYPE: DNA
<213> ORGANISM: primer prx2+

<400> SEQUENCE: 4
cttccaaata tcaactcaat                                               20

<210> SEQ ID NO 5
<211> LENGTH: 20
<212> TYPE: DNA
<213> ORGANISM: primer prx6-

<400> SEQUENCE: 5
taaagttgga aagaaagta                                                20

<210> SEQ ID NO 6
<211> LENGTH: 20
<212> TYPE: DNA
<213> ORGANISM: primer prx9

<400> SEQUENCE: 6
atgcatgcag gttttcagt                                                20

<210> SEQ ID NO 7
<211> LENGTH: 20
<212> TYPE: DNA
<213> ORGANISM: primer prx10-

<400> SEQUENCE: 7
ttgctcgctt tctattgtat                                               20

<210> SEQ ID NO 8
<211> LENGTH: 20
<212> TYPE: DNA
<213> ORGANISM: primer prx12+

<400> SEQUENCE: 8
tcttcgatgc ttcttcacc                                                20

<210> SEQ ID NO 9
<211> LENGTH: 21
<212> TYPE: DNA
<213> ORGANISM: primer prx29+

<400> SEQUENCE: 9
cataaacaat acgtacgtga t                                             21

<210> SEQ ID NO 10
<211> LENGTH: 1031
<212> TYPE: DNA
<213> ORGANISM: Glycine max

<400> SEQUENCE: 10

```
tttcatgatt gctttgttca aggttgtgat ggatcagttt tactgaacaa cactgataca      60
atagaaagcg agcaagatgc acttccaaat atcaactcaa taagaggatt ggacgttgtc     120
aatgacatca agacagcggt ggaaaatagt tgtccagaca cagtttcttg tgctgatatt     180
cttgctattg cagctgaaat agcttctgtt gctggggagga ggtcaggatg ccagttcca     240 ttaggaagaa gggacagctt aacagcaaac cgaaccctg caaatcaaaa ccttccagca     300
cctttcttca acctcactca acttaaagct tcctttgctg ttcaaggtct caacacccctt    360 gatttagtta cactctcagg tggtcatacg tctggaagag ctcggtgcag tacattcata    420
aaccgattat acaacttcag caacactgga ctgatccact ggacacaac atacttagaa     480 gtattgcgtg caagatgccc ccagaatgca actggggata acctcaccaa tttggacctg    540
agcacacctg atcaatttga caacagatac tactccaatc ttctgcagct caatggctta    600
cttcagagtg accaagaacg tttctccact cctggtgctg ataccattcc attgtcaata    660
gcttcagcga accagaatac tttcttttcc aactttagag tttcaatgat aaaaatgggt    720
aatattggag tgctgactgg ggatgaagga gaaattcgct tgcaatgtaa ttttgtgaat    780
ggagactcgt ttggattagc tagtgtggcg tccaaagatg ctaaacaaaa gcttgttgct    840
caatctaaat aaaccaataa ttaatgggga tgtcgatgct agctacgatg taaaggcaaa    900
ttaggttgaa acctctttgc tagctatatt gaaataaacc aaaggagtag tgtcgatgtc    960
aattcgattt tgccatgtac ctcttggaat attatgtaat aattatttga atctcaaaaa    1020
aaaaaaaaaa a                                                          1031

<210> SEQ ID NO 11
<211> LENGTH: 1200
<212> TYPE: DNA
<213> ORGANISM: Medicago sativa

<400> SEQUENCE: 11
ggcaaacaat gaactcccctt cgtgctgtag caatagcttt gtgctgtatt gtggttgtgc     60
ttggagggtt acccttctct tcaaatgcgc aacttgatcc atcctttac aggaacactt     120 gtccaaatgt tagttccatt gttcgtgaag tcataaggag tgtttctaag aaagatcctc    180
gtatgcttgc tagtcttgtc aggcttcact ttcatgactg ttttgttcaa ggttgtgatg    240
catcagtttt actaaacaaa actgataccg ttgtgagtga acaagatgct tttccaaaca    300
gaaactcatt aagaggtttg gatgttgtga atcaaatcaa aacagctgtg aaaaggctt     360 gtcctaacac agtttcttgt gctgatattc ttgctctttc tgctgaatta tcatctacac    420
tggcagatgg tcctgactgg aaggttcctt taggaagaag agatggttta acggcaaacc    480
agttacttgc taatcaaaat cttccagctc ctttcaatac tactgatcaa cttaaagctg    540
catttgctgc tcaaggtctc gatactactg atctggttgc actctccggt gctcatacat    600
ttggaagagc tcattgctct ttatttgtta gccgattgta caacttcagc ggtacgggaa    660
gtcccgatcc aactcttaac acaacttact tacaacaatt gcgcacaata tgtcccaatg    720
gtggacctgg cacgaacctt accaatttcg atccaacgac tcctgataaa tttgacaaga    780
actattactc taatcttcaa gtgaaaaaag gtttgcttca aagtgatcaa gagttgttct    840
caacatctgg ttcagatacc attagcattg tcaacaaatt cgcaaccgat caaaagctt     900 tttttgagag ctttagggct gctatgatca aaatgggaaa tattggtgtg ttaaccggga    960
accaaggaga gattagaaaa caatgcaact ttgttaattc aaaatcagca gaacttggtc    1020
ttatcaatgt tgcctcagca gattcatctg aggagggtat ggttagctca atgtaaatgt    1080
```

```
agtgattgga agcaactaat aaattaagaa gctataacta tgcacattca tggtatgtgt    1140
gagatagtta ttagatgctt tgtgagcaaa aatcttttgg atttcatttg aagtgtttct    1200
```

<210> SEQ ID NO 12
<211> LENGTH: 1200
<212> TYPE: DNA
<213> ORGANISM: Medicago sativa

<400> SEQUENCE: 12

```
gctcttcaaa acaatgaact ccttagcaac ttctatgtgg tgtgttgtgc ttttagttgt      60
gcttggagga ctacccttt cctcagatgc acaacttagt cccactttt acagcaaaac     120
gtgtccaact gttagttcca ttgttagcaa tgtcttaaca aacgtttcta agacagatcc    180
tcgcatgctt gctagtctcg tcaggcttca ctttcatgac tgttttgttc tgggatgtga    240
tgcctcagtt tgctgaaca atactgctac aatcgtaagc gaacaacaag cttttccaaa     300
taacaactct ctaagaggtt tggatgttgt gaatcagatc aaactggctg tagaagtgcc    360
ttgtcctaac acagtttctt gtgctgatat tcttgcactt gctgctcaag catcctctgt    420
tctggcacaa ggtcctagtt ggacggttcc tttaggaaga agggatggtt taaccgcaaa    480
ccgaacactt gcaaatcaaa atcttccggc tccattcaat tccttggatc aacttaaagc    540
tgcatttact gctcaaggcc tcaatactac tgatctagtt gcactctcgg gtgctcatac    600
atttggaaga gctcattgcg cacaatttgt tagtcgattg tacaacttca gcagtactgg    660
aagtcccgat ccaactctta acacaactta cttacaacaa ctgcgcacaa tatgtcccaa    720
tggtggacct ggcacaaacc ttaccaattt cgatccaacg actcctgata aatttgacaa    780
gaactattac tccaatcttc aagtgaaaaa gggtttgctc caaagtgatc aagagttgtt    840
ctcaacttct ggtgcagata ccattagcat tgtcaacaaa ttcagcaccg atcaaaatgc    900
tttctttgag agctttaagg ctgcaatgat taaaatgggc aatattggtg tgctaacagg    960
gacaaaagga gagattagaa acaatgcaa ctttgtgaac tttgtgaact caaattctgc    1020
agaactagat ttagccacca tagcatccat agtagaatca ttagaggatg gtattgctag   1080
tgtaatataa ataaattagc gtaaatgcac ttattgaaat cttgtgacta gatgccacta   1140
ataaataagt tataactagg cacatttcat gtcacttgaa atttcatgcc tgtatatgag   1200
```

<210> SEQ ID NO 13
<211> LENGTH: 1200
<212> TYPE: DNA
<213> ORGANISM: Medicago sativa

<400> SEQUENCE: 13

```
ctccttagca acttctatgt ggtgtgttgt gcttttagtt gtgcttggag gactaccctt      60
ttcctcagat gcacaactta gtcccacttt ttacagcaaa acgtgtccaa ctgttagttc    120
cattgttagc aatgtcttaa caaacgtttc taagacagat cctcgcatgc ttgctagtct    180
cgtcaggctt cactttcatg actgttttgt tctgggatgt gatgcctcag ttttgctgaa    240
caatactgct acaatcgtaa gcgaacaaca agcttttcca aataacaact ctctaagggg    300
tttggatgtt gtgaatcaga tcaaaactgc tgtagaaagt gcttgtccta acacagtttc    360
ttgtgctgat attcttgcac ttgctcaagc atcctctgtt ctggcacaag gtcctagttg    420
gacggttcct ttaggaagaa gggatggttt aaccgcaaac cgaacacttg caaatcaaaa    480
tcttccggct ccattcaatt ccttggatca ccttaaactg catttgactg ctcaaggcct    540
```

-continued

```
cattactcct gttctagttg ccctctcggg tgctcataca tttggaagag ctcattgcgc      600
acaatttgtt agtcgattgt acaacttcag cagtactgga agtcccgatc caactcttaa      660
cacaacttac ttacaacaac tgcgcacaat atgtcccaat ggtggacctg gcacaaacct      720
taccaatttc gatccaacga ctcctgataa atttgacaag aactattact ccaatcttca      780
agtgaaaaag ggtttgctcc aaagtgatca agagttgttc tcaacttctg gtgcagatac      840
cattagcatt gtcgacaaat tcagcaccga tcaaaatgct ttctttgaga gctttaaggc      900
tgcaatgatt aaaatgggca atattggtgt gctaacaggg acaaaaggag agattagaaa      960
acaatgcaac tttgtgaact caattctgc agaactagat ttagccacca tagcatccat      1020
agtagaatca ttagaggatg gaattgctag tgtaatataa ataaattagc gaaaatgcac     1080
ttattgaaat cttgtgacta gatcccacta ataaataagt tataactagg cacatttcat     1140
gtcacttgaa atcctatgcc ttgtatatta gaggacgtgt tcttcttggt attatactat     1200
```

<210> SEQ ID NO 14
<211> LENGTH: 1200
<212> TYPE: DNA
<213> ORGANISM: Medicago sativa

<400> SEQUENCE: 14

```
aatgcttggt ctaagtgcaa cagcttttg ctgtatggtg tttgtgctaa ttggaggagt       60
acccttttca aatgcacaac tagatccttc attttacaac agtacatgtt ctaatcttga      120
ttcaatcgta cgtggtgtgc tcacaaatgt ttcacaatct gatcccagaa tgcttggtag      180
tctcatcagg ctacattttc atgactgttt tgttcaaggt tgcgatgcct cgattttgct      240
gaacgatacg gctacaatag tgagcgagca aagtgcacca ccaaataaca actcccataag     300 aggtttggat gtgataaacc agatcaaaac agcggtggaa aatgcttgtc ctaacacagt      360
ttcttgtgct gatattcttg ctctttctgc tgaaatatca tctgatctgg caaatggtcc      420
tacttggcaa gttccattag aagaaggga tagtttgaca gcaaataatt cccttgcagc      480
tcaaaatctt cctgccccca ctttcaacct tactcgacta aaatctaact ttgataatca      540
aaacctcagt actactgatc tagttgcact ctcaggtggc catacaattg aagaggtca      600 atgcagattt tcgttgatc gattatacaa tttcagcaac actggaaacc ccgattcaac       660
tcttaacacg acctatttac aaacattgca agcaatatgt cccaatggtg gacctggtac      720
aaacctaacc gatttggacc caaccacacc agatacattt gactccaact actactccaa      780
tctccaagtt ggaaagggct tgtttcagag tgaccaagag ctttttttcca gaaatggttc      840 tgacactatt tctattgtca atagtttcgc caataatcaa actctcttct ttgaaaattt      900
tgtagcctca atgataaaaa tgggtaatat tggagtttta actggatctc aaggtgaaat      960
tagaacacag tgtaatgctg tgaatgggaa ttcttctgga ttggctactg tagtcaccaa      1020
agaatcatca gaagatggaa tggctagctc attctaaata taagcttgga aaatattgaa      1080
gaggttctat aattttgtgc atacatatat ggtatgtgca tgtggtgtat tatgttttg      1140 ttatgttctt caagttgatc agggactgta gaagctccct aataatattt gtgtcaaagt      1200
```

<210> SEQ ID NO 15
<211> LENGTH: 283
<212> TYPE: PRT
<213> ORGANISM: Glycine max

<400> SEQUENCE: 15

```
Phe His Asp Cys Phe Val Gln Gly Cys Asp Gly Ser Val Leu Leu Asn
1               5                   10                  15

Asn Thr Asp Thr Ile Glu Ser Glu Gln Asp Ala Leu Pro Asn Ile Asn
            20                  25                  30

Ser Ile Arg Gly Leu Asp Val Val Asn Asp Ile Lys Thr Ala Val Glu
        35                  40                  45

Asn Ser Cys Pro Asp Thr Val Ser Cys Ala Asp Ile Leu Ala Ile Ala
    50                  55                  60

Ala Glu Ile Ala Ser Val Ala Gly Arg Arg Ser Gly Trp Pro Val Pro
65                  70                  75                  80

Leu Gly Arg Arg Asp Ser Leu Thr Ala Asn Arg Thr Leu Ala Asn Gln
                85                  90                  95

Asn Leu Pro Ala Pro Phe Phe Asn Leu Thr Gln Leu Lys Ala Ser Phe
            100                 105                 110

Ala Val Gln Gly Leu Asn Thr Leu Asp Leu Val Thr Leu Ser Gly Gly
        115                 120                 125

His Thr Ser Gly Arg Ala Arg Cys Ser Thr Phe Ile Asn Arg Leu Tyr
    130                 135                 140

Asn Phe Ser Asn Thr Gly Leu Ile His Leu Asp Thr Thr Tyr Leu Glu
145                 150                 155                 160

Val Leu Arg Ala Arg Cys Pro Gln Asn Ala Thr Gly Asp Asn Leu Thr
                165                 170                 175

Asn Leu Asp Leu Ser Thr Pro Asp Gln Phe Asp Asn Arg Tyr Tyr Ser
            180                 185                 190

Asn Leu Leu Gln Leu Asn Gly Leu Leu Gln Ser Asp Gln Glu Arg Phe
        195                 200                 205

Ser Thr Pro Gly Ala Asp Thr Ile Pro Leu Ser Ile Ala Ser Ala Asn
    210                 215                 220

Gln Asn Thr Phe Phe Ser Asn Phe Arg Val Ser Met Ile Lys Met Gly
225                 230                 235                 240

Asn Ile Gly Val Leu Thr Gly Asp Glu Gly Glu Ile Arg Leu Gln Cys
                245                 250                 255

Asn Phe Val Asn Gly Asp Ser Phe Gly Leu Ala Ser Val Ala Ser Lys
            260                 265                 270

Asp Ala Lys Gln Lys Leu Val Ala Gln Ser Lys
        275                 280

<210> SEQ ID NO 16
<211> LENGTH: 355
<212> TYPE: PRT
<213> ORGANISM: Medicago sativa

<400> SEQUENCE: 16

Met Asn Ser Leu Arg Ala Val Ala Ile Ala Leu Cys Cys Ile Val Val
1               5                   10                  15

Val Leu Gly Gly Leu Pro Phe Ser Ser Asn Ala Gln Leu Asp Pro Ser
            20                  25                  30

Phe Tyr Arg Asn Thr Cys Pro Asn Val Ser Ser Ile Val Arg Glu Val
        35                  40                  45

Ile Arg Ser Val Ser Lys Lys Asp Pro Arg Met Leu Ala Ser Leu Val
    50                  55                  60

Arg Leu His Phe His Asp Cys Phe Val Gln Gly Cys Asp Ala Ser Val
65                  70                  75                  80

Leu Leu Asn Lys Thr Asp Thr Val Val Ser Glu Gln Asp Ala Phe Pro
                85                  90                  95
```

```
Asn Arg Asn Ser Leu Arg Gly Leu Asp Val Val Asn Gln Ile Lys Thr
            100                 105                 110

Ala Val Glu Lys Ala Cys Pro Asn Thr Val Ser Cys Ala Asp Ile Leu
            115                 120                 125

Ala Leu Ser Ala Glu Leu Ser Ser Thr Leu Ala Asp Gly Pro Asp Trp
            130                 135                 140

Lys Val Pro Leu Gly Arg Arg Asp Gly Leu Thr Ala Asn Gln Leu Leu
145                 150                 155                 160

Ala Asn Gln Asn Leu Pro Ala Pro Phe Asn Thr Thr Asp Gln Leu Lys
                165                 170                 175

Ala Ala Phe Ala Ala Gln Gly Leu Asp Thr Thr Asp Leu Val Ala Leu
            180                 185                 190

Ser Gly Ala His Thr Phe Gly Arg Ala His Cys Ser Leu Phe Val Ser
            195                 200                 205

Arg Leu Tyr Asn Phe Ser Gly Thr Gly Ser Pro Asp Pro Thr Leu Asn
            210                 215                 220

Thr Thr Tyr Leu Gln Gln Leu Arg Thr Ile Cys Pro Asn Gly Gly Pro
225                 230                 235                 240

Gly Thr Asn Leu Thr Asn Phe Asp Pro Thr Thr Pro Asp Lys Phe Asp
                245                 250                 255

Lys Asn Tyr Tyr Ser Asn Leu Gln Val Lys Lys Gly Leu Leu Gln Ser
            260                 265                 270

Asp Gln Glu Leu Phe Ser Thr Ser Gly Ser Asp Thr Ile Ser Ile Val
            275                 280                 285

Asn Lys Phe Ala Thr Asp Gln Lys Ala Phe Phe Glu Ser Phe Arg Ala
            290                 295                 300

Ala Met Ile Lys Met Gly Asn Ile Gly Val Leu Thr Gly Asn Gln Gly
305                 310                 315                 320

Glu Ile Arg Lys Gln Cys Asn Phe Val Asn Ser Lys Ser Ala Glu Leu
                325                 330                 335

Gly Leu Ile Asn Val Ala Ser Ala Asp Ser Ser Glu Glu Gly Met Val
            340                 345                 350

Ser Ser Met
        355

<210> SEQ ID NO 17
<211> LENGTH: 358
<212> TYPE: PRT
<213> ORGANISM: Medicago sativa

<400> SEQUENCE: 17

Met Asn Ser Leu Ala Thr Ser Met Trp Cys Val Val Leu Leu Val Val
1               5                   10                  15

Leu Gly Gly Leu Pro Phe Ser Ser Asp Ala Gln Leu Ser Pro Thr Phe
            20                  25                  30

Tyr Ser Lys Thr Cys Pro Thr Val Ser Ser Ile Val Ser Asn Val Leu
            35                  40                  45

Thr Asn Val Ser Lys Thr Asp Pro Arg Met Leu Ala Ser Leu Val Arg
50                  55                  60

Leu His Phe His Asp Cys Phe Val Leu Gly Cys Asp Ala Ser Val Leu
65                  70                  75                  80

Leu Asn Asn Thr Ala Thr Ile Val Ser Glu Gln Gln Ala Phe Pro Asn
                85                  90                  95
```

```
Asn Asn Ser Leu Arg Gly Leu Asp Val Val Asn Gln Ile Lys Leu Ala
            100                 105                 110
Val Glu Val Pro Cys Pro Asn Thr Val Ser Cys Ala Asp Ile Leu Ala
        115                 120                 125
Leu Ala Ala Gln Ala Ser Ser Val Leu Ala Gln Gly Pro Ser Trp Thr
    130                 135                 140
Val Pro Leu Gly Arg Arg Asp Gly Leu Thr Ala Asn Arg Thr Leu Ala
145                 150                 155                 160
Asn Gln Asn Leu Pro Ala Pro Phe Asn Ser Leu Asp Gln Leu Lys Ala
                165                 170                 175
Ala Phe Thr Ala Gln Gly Leu Asn Thr Thr Asp Leu Val Ala Leu Ser
            180                 185                 190
Gly Ala His Thr Phe Gly Arg Ala His Cys Ala Gln Phe Val Ser Arg
        195                 200                 205
Leu Tyr Asn Phe Ser Ser Thr Gly Ser Pro Asp Pro Thr Leu Asn Thr
    210                 215                 220
Thr Tyr Leu Gln Gln Leu Arg Thr Ile Cys Pro Asn Gly Gly Pro Gly
225                 230                 235                 240
Thr Asn Leu Thr Asn Phe Asp Pro Thr Thr Pro Asp Lys Phe Asp Lys
                245                 250                 255
Asn Tyr Tyr Ser Asn Leu Gln Val Lys Lys Gly Leu Leu Gln Ser Asp
            260                 265                 270
Gln Glu Leu Phe Ser Thr Ser Gly Ala Asp Thr Ile Ser Ile Val Asn
        275                 280                 285
Lys Phe Ser Thr Asp Gln Asn Ala Phe Phe Glu Ser Phe Lys Ala Ala
    290                 295                 300
Met Ile Lys Met Gly Asn Ile Gly Val Leu Thr Gly Thr Lys Gly Glu
305                 310                 315                 320
Ile Arg Lys Gln Cys Asn Phe Val Asn Phe Val Asn Ser Asn Ser Ala
                325                 330                 335
Glu Leu Asp Leu Ala Thr Ile Ala Ser Ile Val Glu Ser Leu Glu Asp
            340                 345                 350
Gly Ile Ala Ser Val Ile
            355

<210> SEQ ID NO 18
<211> LENGTH: 347
<212> TYPE: PRT
<213> ORGANISM: Medicago sativa

<400> SEQUENCE: 18

Met Trp Cys Val Val Leu Leu Val Val Leu Gly Gly Leu Pro Phe Ser
1               5                   10                  15
Ser Asp Ala Gln Leu Ser Pro Thr Phe Tyr Ser Lys Thr Cys Pro Thr
            20                  25                  30
Val Ser Ser Ile Val Ser Asn Val Leu Thr Asn Val Ser Lys Thr Asp
        35                  40                  45
Pro Arg Met Leu Ala Ser Leu Val Arg Leu His Phe His Asp Cys Phe
    50                  55                  60
Val Leu Gly Cys Asp Ala Ser Val Leu Leu Asn Asn Thr Ala Thr Ile
65                  70                  75                  80
Val Ser Glu Gln Gln Ala Phe Pro Asn Asn Asn Ser Leu Arg Gly Leu
                85                  90                  95
Asp Val Val Asn Gln Ile Lys Thr Ala Val Glu Ser Ala Cys Pro Asn
            100                 105                 110
```

```
Thr Val Ser Cys Ala Asp Ile Leu Ala Leu Ala Gln Ala Ser Ser Val
            115                 120                 125

Leu Ala Gln Gly Pro Ser Trp Thr Val Pro Leu Gly Arg Arg Asp Gly
        130                 135                 140

Leu Thr Ala Asn Arg Thr Leu Ala Asn Gln Asn Leu Pro Ala Pro Phe
145                 150                 155                 160

Asn Ser Leu Asp His Leu Lys Leu His Leu Thr Ala Gln Gly Leu Ile
                165                 170                 175

Thr Pro Val Leu Val Ala Leu Ser Gly Ala His Thr Phe Gly Arg Ala
            180                 185                 190

His Cys Ala Gln Phe Val Ser Arg Leu Tyr Asn Phe Ser Ser Thr Gly
        195                 200                 205

Ser Pro Asp Pro Thr Leu Asn Thr Thr Tyr Leu Gln Gln Leu Arg Thr
210                 215                 220

Ile Cys Pro Asn Gly Gly Pro Gly Thr Asn Leu Thr Asn Phe Asp Pro
225                 230                 235                 240

Thr Thr Pro Asp Lys Phe Asp Lys Asn Tyr Tyr Ser Asn Leu Gln Val
                245                 250                 255

Lys Lys Gly Leu Leu Gln Ser Asp Gln Glu Leu Phe Ser Thr Ser Gly
            260                 265                 270

Ala Asp Thr Ile Ser Ile Val Asp Lys Phe Ser Thr Asp Gln Asn Ala
        275                 280                 285

Phe Phe Glu Ser Phe Lys Ala Ala Met Ile Lys Met Gly Asn Ile Gly
290                 295                 300

Val Leu Thr Gly Thr Lys Gly Glu Ile Arg Lys Gln Cys Asn Phe Val
305                 310                 315                 320

Asn Ser Asn Ser Ala Glu Leu Asp Leu Ala Thr Ile Ala Ser Ile Val
                325                 330                 335

Glu Ser Leu Glu Asp Gly Ile Ala Ser Val Ile
            340                 345

<210> SEQ ID NO 19
<211> LENGTH: 351
<212> TYPE: PRT
<213> ORGANISM: Medicago sativa

<400> SEQUENCE: 19

Met Leu Gly Leu Ser Ala Thr Ala Phe Cys Cys Met Val Phe Val Leu
1               5                   10                  15

Ile Gly Gly Val Pro Phe Ser Asn Ala Gln Leu Asp Pro Ser Phe Tyr
            20                  25                  30

Asn Ser Thr Cys Ser Asn Leu Asp Ser Ile Val Arg Gly Val Leu Thr
        35                  40                  45

Asn Val Ser Gln Ser Asp Pro Arg Met Leu Gly Ser Leu Ile Arg Leu
    50                  55                  60

His Phe His Asp Cys Phe Val Gln Gly Cys Asp Ala Ser Ile Leu Leu
65                  70                  75                  80

Asn Asp Thr Ala Thr Ile Val Ser Glu Gln Ser Ala Pro Pro Asn Asn
                85                  90                  95

Asn Ser Ile Arg Gly Leu Asp Val Ile Asn Gln Ile Lys Thr Ala Val
            100                 105                 110

Glu Asn Ala Cys Pro Asn Thr Val Ser Cys Ala Asp Ile Leu Ala Leu
        115                 120                 125

Ser Ala Glu Ile Ser Ser Asp Leu Ala Asn Gly Pro Thr Trp Gln Val
    130                 135                 140
```

```
Pro Leu Gly Arg Arg Asp Ser Leu Thr Ala Asn Asn Ser Leu Ala Ala
145                 150                 155                 160

Gln Asn Leu Pro Ala Pro Thr Phe Asn Leu Thr Arg Leu Lys Ser Asn
                165                 170                 175

Phe Asp Asn Gln Asn Leu Ser Thr Thr Asp Leu Val Ala Leu Ser Gly
                180                 185                 190

Gly His Thr Ile Gly Arg Gly Gln Cys Arg Phe Phe Val Asp Arg Leu
                195                 200                 205

Tyr Asn Phe Ser Asn Thr Gly Asn Pro Asp Ser Thr Leu Asn Thr Thr
                210                 215                 220

Tyr Leu Gln Thr Leu Gln Ala Ile Cys Pro Asn Gly Gly Pro Gly Thr
225                 230                 235                 240

Asn Leu Thr Asp Leu Asp Pro Thr Thr Pro Asp Thr Phe Asp Ser Asn
                245                 250                 255

Tyr Tyr Ser Asn Leu Gln Val Gly Lys Gly Leu Phe Gln Ser Asp Gln
                260                 265                 270

Glu Leu Phe Ser Arg Asn Gly Ser Asp Thr Ile Ser Ile Val Asn Ser
                275                 280                 285

Phe Ala Asn Asn Gln Thr Leu Phe Phe Glu Asn Phe Val Ala Ser Met
290                 295                 300

Ile Lys Met Gly Asn Ile Gly Val Leu Thr Gly Ser Gln Gly Glu Ile
305                 310                 315                 320

Arg Thr Gln Cys Asn Ala Val Asn Gly Asn Ser Ser Gly Leu Ala Thr
                325                 330                 335

Val Val Thr Lys Glu Ser Ser Glu Asp Gly Met Ala Ser Ser Phe
                340                 345                 350

<210> SEQ ID NO 20
<211> LENGTH: 22
<212> TYPE: DNA
<213> ORGANISM: Medicago sativa

<400> SEQUENCE: 20
taaaatcata tcagcttact cc                                              22
```